(12) United States Patent
Ducoux et al.

(10) Patent No.: US 7,687,537 B2
(45) Date of Patent: *Mar. 30, 2010

(54) N-[(4,5-DIPHENYL-2-THIENYL)METHYL]AMINE DERIVATIVES, THEIR PREPARATION AND THEIR THERAPEUTIC APPLICATION

(75) Inventors: Jean-Philippe Ducoux, Combaillaux (FR); Francis Barth, Saint Georges d'Orques (FR); Murielle Rinaldi-Carmona, Saint Georges d'Orques (FR); Christian Congy, Saint Gely du Fesc (FR)

(73) Assignee: Sanofi-Aventis, Paris (FR)

( * ) Notice: Subject to any disclaimer, the term of this patent is extended or adjusted under 35 U.S.C. 154(b) by 42 days.

This patent is subject to a terminal disclaimer.

(21) Appl. No.: 11/832,162

(22) Filed: Aug. 1, 2007

(65) Prior Publication Data

US 2008/0009543 A1 Jan. 10, 2008

Related U.S. Application Data

(63) Continuation of application No. PCT/FR2006/000219, filed on Feb. 1, 2006.

(30) Foreign Application Priority Data

Feb. 9, 2005 (FR) .................................. 05 01366

(51) Int. Cl.
*A61K 31/38* (2006.01)
*C07D 333/08* (2006.01)
(52) U.S. Cl. ........................................ 514/438; 549/80
(58) Field of Classification Search ........................ None
See application file for complete search history.

(56) References Cited

FOREIGN PATENT DOCUMENTS

| | | |
|---|---|---|
| EP | 0576357 | 12/1993 |
| WO | WO 2005/035488 | 4/2005 |
| WO | WO 2005/073197 | 8/2005 |

OTHER PUBLICATIONS

Chewla et al., CRIPS vol. 5, No. 1, Jan.-Mar. 2004, p. 9-12.*
Newman et al., DDT vol. 8, Oct. 2003, p. 898-890.*
Rimonabant, http://www.norml.org/index.cfm?Group_ID=7282&wtm_format=print (2 pages).*
Anorexia, http://www.mayoclinic.com/health/anorexia/DS00606/DSECTION=8.*
Zips et al, "new anticancer agents: in vitro and in vivo", in vivo, 2005, 19, 1-7.*
Palmer, S. L., et. al. Cannabinergic Ligands, Chemistry and Physics of Lipids vol. 121, (2002) pp. 3-19.

* cited by examiner

*Primary Examiner*—Golam M. M. Shameem
*Assistant Examiner*—Sun Jae Y Loewe
(74) *Attorney, Agent, or Firm*—Balaram Gupta

(57) ABSTRACT

The subject of the present invention is compounds corresponding to formula (I):

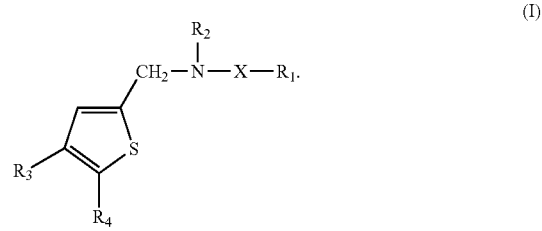

Wherein X, $R_1$, $R_2$, $R_3$ and $R_4$ are as described herein. The invention also relates to a method for the preparation and application of said compounds as cannabinoid CB1 receptor antagonists.

9 Claims, No Drawings

N-[(4,5-DIPHENYL-2-THIENYL)METHYL]AMINE DERIVATIVES, THEIR PREPARATION AND THEIR THERAPEUTIC APPLICATION

CROSS REFERENCE TO RELATED APPLICATIONS

This application is a continuation of International application No. PCT/FR2006/000,219, filed Feb. 1, 2006, which is incorporated herein by reference in its entirety; which claims the benefit of priority of French Patent Application No. 05/01, 366, filed Feb. 9, 2005.

BACKGROUND OF THE INVENTION

1. Field of the Invention

The subject of the present invention is substituted N-[(4,5-diphenyl-2-thienyl)methyl]amine derivatives, their preparation and their therapeutic application.

2. Description of the Art

Diphenylpyrazole derivatives having affinity for the $CB_1$ cannabinoid receptors have been described in particular in patents U.S. Pat. No. 5,624,941, EP 0 576 357, EP 0 656 354 and EP 1 150 961 and WO 2005/073 197.

4,5-Diarylthiophene derivatives having anti-inflammatory and analgesic properties are described in international application WO 91/19708 and in patent applications EP0 024 042, EP 0 055 470, EP 0 055 471 and U.S. Pat. No. 4,432,974.

Thiophene-2-carboxamide derivatives are described in international application WO 2005/035488.

SUMMARY OF THE INVENTION

Novel substituted N-[(4,5-diphenyl-2-thienyl)methyl]amine derivatives which possess $CB_1$ cannabinoid receptor antagonist properties have now been found.

The subject of the present invention is compounds corresponding to the formula:

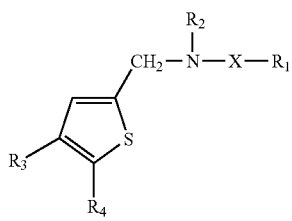
(I)

in which:
X represents a group

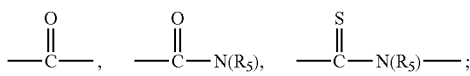

$R_1$ represents:
- a $(C_6-C_{12})$alkyl;
- a nonaromatic $(C_3-C_{12})$ carbocyclic radical which is unsubstituted or substituted once or several times with a $(C_1-C_4)$alkyl;
- a methyl which is substituted with a nonaromatic $C_3-C_{12}$ carbocyclic radical and which is unsubstituted or substituted once or several times on the carbocycle with a $(C_1-C_4)$alkyl;
- a phenyl which is mono-, di- or -trisubstituted with substituents independently chosen from a halogen atom, a $(C_1-C_4)$alkyl, a $(C_1-C_4)$alkoxy, a $(C_1-C_4)$alkylamino, a di-$(C_1-C_4)$alkylamino, a cyano, a trifluoromethyl radical, a trifluoromethoxy radical, an $S(O)_n$Alk group, a $(C_1-C_4)$alkylcarbonyl group, a methylenedioxy; or from a phenyl, phenoxy, pyrrolyl, imidazolyl, pyridyl or pyrazolyl radical, the said radicals being unsubstituted or substituted once or several times with a $(C_1-C_4)$alkyl;
- a benzyl which is mono- or disubstituted on the phenyl with substituents independently chosen from a halogen atom, a $(C_1-C_4)$alkyl, a $(C_1-C_4)$alkoxy, a trifluoromethyl radical, a (trifluoromethyl)thio radical, or substituted at the alpha-position with one or two similar or different groups chosen from a $(C_1-C_4)$alkyl, a $(C_3-C_7)$cycloalkyl, or a pyrrolyl radical;
- a phenethyl which is unsubstituted or mono- or disubstituted on the phenyl with substituents independently chosen from the halogen atom, a $(C_1-C_4)$alkyl, a $(C_1-C_4)$alkoxy, a trifluoromethyl radical;
- a 1,2,3,4-tetrahydronaphthyl or a 5,6,7,8-tetrahydronaphthyl which is unsubstituted or mono- or disubstituted with substituents independently chosen from a $(C_1-C_4)$alkyl, a $(C_1-C_4)$alkoxy, a trifluoromethyl radical;
- a benzhydryl; a benzhydrylmethyl;

$R_2$ represents a hydrogen atom or a $(C_1-C_3)$alkyl;
$R_3$ represents a phenyl which is unsubstituted or mono-, di- or trisubstituted with substituents independently chosen from a halogen atom, a $(C_1-C_4)$alkyl, a $(C_1-C_4)$alkoxy, a trifluoromethyl radical or an $S(O)_n$Alk group;
$R_4$ represents a phenyl which is unsubstituted or mono-, di- or trisubstituted with substituents independently chosen from a halogen atom, a $(C_1-C_4)$alkyl, a $(C_1-C_4)$alkoxy, a trifluoromethyl radical or an $S(O)_n$Alk group;
$R_5$ represents a hydrogen atom or a $(C_1-C_3)$alkyl;
n represents 0, 1 or 2;
Alk represents a $(C_1-C_4)$alkyl.

The compounds of formula (I) may contain one or more asymmetric carbon atoms. They can therefore exist in the form of enantiomers or diastereo isomers. These enantiomers, diastereo isomers and mixtures thereof, including racemic mixtures, form part of the invention.

The compounds of formula (I) can exist in the form of hydrates or solvates, namely in the form of associations or combinations with one or more water molecules or with a solvent. Such hydrates and solvates also form part of the invention.

DETAILED DESCRIPTION OF THE INVENTION

The expression halogen is understood to mean a bromine, chlorine, fluorine or iodine atom.

The expression $(C_1-C_3)$alkyl or respectively $(C_1-C_4)$alkyl, or $(C_6-C_{12})$alkyl is understood to mean a linear or branched alkyl radical of one to three carbon atoms or respectively of one to four carbon atoms, or of six to twelve carbon atoms, such as the methyl, ethyl, propyl, isopropyl, butyl, isobutyl, sec-butyl, tert-butyl, hexyl, isohexyl, heptyl, octyl, nonyl, decyl, undecyl or dodecyl radical.

The expression $(C_1-C_4)$alkoxy is understood to mean a linear or branched alkoxy radical of one to four carbon atoms such as the methoxy, ethoxy, propoxy, isopropoxy, butoxy, sec-butoxy, or tert-butoxy radical.

The expression $(C_3-C_7)$cycloalkyl is understood to mean a cyclic alkyl group of 3 to 7 carbon atoms, such as the cyclopropyl, cyclobutyl, cyclopentyl, cyclohexyl, or cycloheptyl group.

The nonaromatic $C_3-C_{12}$ carbocyclic radicals comprise the fused, bridged or spiro mono- or polycyclic radicals. The monocyclic radicals include the cycloalkyls, for example cyclopropyl, cyclobutyl, cyclopentyl, cyclohexyl, cycloheptyl, and cyclooctyl. The fused, bridged or spiro di- or tricyclic radicals include for example the norbornyl, bornyl, isobornyl, noradamantyl, adamantyl, spiro[5.5]undecyl, bicyclo[2.2.1]heptyl, bicyclo[3.2.1]octyl, bicyclo[3.1.1]heptyl, and bicyclo-[2.2.1]hept-5-en-2-yl radicals.

Among the compounds of formula (I) which are the subject of the invention are:
the compounds of formula (IA) in which —X— represents a —CO— radical and the substituents $R_1$ to $R_4$ are as defined for the compounds of formula (I);
the compounds of formula (IB) in which —X— represents a —CON($R_5$)— radical and the substituents $R_1$ to $R_5$ are as defined for the compounds of formula (I);
the compounds of formula (IC) in which —X— represents a —CSN($R_5$)— radical and to the substituents $R_1$ to $R_5$ are as defined for the compounds of formula (I). According to the present invention, the compounds of formula (I) are preferred in which:
X represents a group

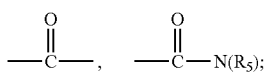

$R_1$ represents:
a $(C_6-C_{12})$alkyl;
a $(C_3-C_7)$cycloalkyl which is unsubstituted or substituted once or several times with a $(C_1-C_3)$alkyl group;
a $(C_3-C_7)$cycloalkylmethyl which is unsubstituted or substituted once or several times on the carbocycle with a $(C_1-C_3)$alkyl;
a phenyl which is mono-, di- or -trisubstituted with substituents independently chosen from a halogen atom, a $(C_1-C_4)$alkoxy, a cyano, a trifluoromethyl radical, a trifluoromethoxy radical, an $S(O)_n$Alk group, a $(C_1-C_4)$alkylcarbonyl group, a phenyl;
a benzyl which is mono- or disubstituted with substituents independently chosen from a halogen atom, a $(C_1-C_4)$alkyl, a $(C_1-C_4)$alkoxy, a trifluoromethyl radical;
$R_2$ represents a hydrogen atom or a $(C_1-C_3)$alkyl;
$R_3$ represents a phenyl which is unsubstituted or mono-, di- or trisubstituted with substituents independently chosen from a halogen atom, a $(C_1-C_4)$alkyl, a $(C_1-C_4)$alkoxy, a trifluoromethyl radical or an $S(O)_n$Alk group;
$R_4$ represents a phenyl which is unsubstituted or mono-, di- or trisubstituted with substituents independently chosen from a halogen atom, a $(C_1-C_4)$alkyl, a $(C_1-C_4)$alkoxy, a trifluoromethyl radical or an $S(O)_n$Alk group;
$R_5$ represents a hydrogen atom or a $(C_1-C_3)$alkyl;
n represents 0, 1 or 2;
Alk represents a $(C_1-C_4)$alkyl;

in the form of a base and in the form of a hydrate or a solvate.

Among the compounds of formula (I), which are the subject of the invention, a first group of compounds consists of the compounds for which:

X represents a —CO— group, a —CONH— group or a —CSNH— group;
and/or $R_1$ represents:
a 1-propylbutyl; a 1-ethylpentyl; a 1-methylpentyl;
a cycloheptyl; a 1-methylcyclopropyl; a cyclobutyl; a cyclopentyl; a cyclohexyl; a 1-methylcyclohexyl; a bicyclo[2.2.1]hept-2-yl; a bicyclo[2.2.1]hept-5-en-2-yl;
a cyclohexylmethyl; a cycloheptylmethyl; a bicyclo[2.2.1]hept-2-ylmethyl;
a 4-bromophenyl; a 4-chlorophenyl; a 2-fluorophenyl; a 3-fluorophenyl; a 4-fluorophenyl; a 3,5-difluorophenyl; a 2,5-difluorophenyl; a 2-methoxyphenyl; a 3-methoxyphenyl; a 3-cyanophenyl; a 4-cyanophenyl; a 3-(trifluoromethyl)-phenyl; a 4-(trifluoromethyl)phenyl: a 4-(trifluoromethoxy)phenyl; a 3-acetylphenyl; a biphenyl-2-yl; a biphenyl-4-yl; a 1,3-benzodioxol-5-yl; a 4-phenoxyphenyl; a 4-(1H-pyrrol-1-yl)phenyl;
a 2-fluorobenzyl; a 3-fluorobenzyl; a 4-fluorobenzyl; a 4-(trifluoromethyl)benzyl; a 4-1[(trifluoromethyl)thio]benzyl; an α-cyclohexylbenzyl; an α-(1H-pyrrol-1-yl)benzyl;
a 4-(trifluoromethyl)phenethyl;
a benzhydryl: a benzhydrylmethyl;
a 1,2,3,4-tetrahydronaphth-2-yl; a 1,2,3,4-tetrahydronaphth-1-yl; a 5,6,7,8-tetrahydronaphth-1-yl;
and/or $R_2$ represents a hydrogen atom or a methyl;
and/or $R_3$ represents a 4-bromophenyl; a 4-chlorophenyl; a 2,4-dichlorophenyl; a 4-methoxyphenyl;
and/or $R_4$ represents a 4-chlorophenyl; a 2,4 dichlorophenyl; a 4-methoxyphenyl;

and their hydrates or their solvates.

Among the compounds of the latter group, there may be mentioned the compounds of formula (I) for which:
X represents a —CO— group, a —CONH— group or a —CSNH— group;
$R_1$ represents:
a 1-propylbutyl; a 1-ethylpentyl; a 1-methylpentyl;
a cycloheptyl; a 1-methylcyclopropyl; a cyclobutyl; a cyclopentyl; a cyclohexyl; a 1-methylcyclohexyl; a bicyclo[2.2.1]hept-2-yl: a bicyclo[2.2.1]hept-5-en-2-yl;
a cyclohexylmethyl; a cycloheptylmethyl; a bicyclo[2.2.1]hept-2-ylmethyl;
a 4-bromophenyl; a 4-chlorophenyl; a 2-fluorophenyl; a 3-fluorophenyl; a 4-fluorophenyl; a 3,5-difluorophenyl; a 2,5-difluorophenyl; a 2-methoxyphenyl; a 3-methoxyphenyl; a 3-cyanophenyl; a 4-cyanophenyl; a 3-(trifluoromethyl)-phenyl; a 4-(trifluoromethyl)phenyl: a 4-(trifluoromethoxy)phenyl; a 3-acetylphenyl; a biphenyl-2-yl; a biphenyl-4-yl; a 1,3-benzodioxol-5-yl; a 4-phenoxyphenyl; a 4-(1H-pyrrol-1-yl)phenyl;
a 2-fluorobenzyl; a 3-fluorobenzyl; a 4-fluorobenzyl; a 4-(trifluoromethyl)benzyl; a 4-[(trifluoromethyl)thio]benzyl; an α-cyclohexylbenzyl; an α-(1H-pyrrol-1-yl)benzyl;
a 4-(trifluoromethyl)phenethyl;
a benzhydryl: a benzhydrylmethyl;
a 1,2,3,4-tetrahydronaphth-2-yl; a 1,2,3,4-tetrahydronaphth-1-yl; a 5,6,7,8-tetrahydronaphth-1-yl;
$R_2$ represents a hydrogen atom or a methyl;
$R_3$ represents a 4-bromophenyl; a 4-chlorophenyl; a 2,4-dichlorophenyl; a 4-methoxyphenyl;

R$_4$ represents a 4-chlorophenyl; a 2,4 dichlorophenyl; a 4-methoxyphenyl;

and their hydrates or their solvates.

Among the compounds of the latter group, there may be mentioned the compounds of formula (I) for which:

X represents a —CO— group or a —CONH— group;

R$_1$ represents:
- a 1-propylbutyl; a 1-ethylpentyl; a 1-methylpentyl;
- a cycloheptyl;
- a cycloheptylmethyl;
- a biphenyl-2-yl;

R$_2$ represents a hydrogen atom or a methyl;

R$_3$ represents a 4-bromophenyl; a 4-chlorophenyl; a 2,4-dichlorophenyl;

R$_4$ represents a 4-chlorophenyl; a 2,4-dichlorophenyl;

and their hydrates or their solvates.

Among the compounds of formula (I), which are the subject of the invention, the following compounds may be mentioned in particular:

N-[[4-(4-chlorophenyl)-5-(2,4-dichlorophenyl)-2-thienyl]methyl]-2-propylpentanamide;
N-[[4-(4-chlorophenyl)-5-(2,4-dichlorophenyl)-2-thienyl]methyl]-2-ethylhexanamide;
N-[[4-(4-chlorophenyl)-5-(2,4-dichlorophenyl)-2-thienyl]methyl]-2-methylhexanamide;
N-[[4-(4-chlorophenyl)-5-(2,4-dichlorophenyl)-2-thienyl]methyl]-cycloheptanecarboxamide;
N-[[4-(4-chlorophenyl)-5-(2,4-dichlorophenyl)-2-thienyl]methyl]-2-cycloheptylacetamide;
N-biphenyl-2-yl-N'-[[4-(4-chlorophenyl)-5-(2,4-dichlorophenyl)-2-thienyl]methyl]urea;
N-[[4-(4-bromophenyl)-5-(2,4-dichlorophenyl)-2-thienyl]methyl]-2-propylpentanamide;
N-[[4-(4-bromophenyl)-5-(2,4-dichlorophenyl)-2-thienyl]methyl]-2-methylhexanamide;
N-[[4-(4-bromophenyl)-5-(2,4-dichlorophenyl)-2-thienyl]methyl]-2-ethylhexanamide;
N-[[4-(4-bromophenyl)-5-(2,4-dichlorophenyl)-2-thienyl]methyl]-cycloheptanecarboxamide;
N-[[4-(4-bromophenyl)-5-(2,4-dichlorophenyl)-2-thienyl]methyl]-N-methylcycloheptanecarboxamide;
N-[[4-(4-bromophenyl)-5-(2,4-dichlorophenyl)-2-thienyl]methyl]-2-cycloheptylacetamide;
N-[[4-(4-bromophenyl)-5-(2,4-dichlorophenyl)-2-thienyl]methyl]-2-cycloheptyl-N-methylacetamide;
N-[[5-(4-chlorophenyl)-4-(2,4-dichlorophenyl)-2-thienyl]methyl]-cycloheptanecarboxamide;
N-[[5-(4-chlorophenyl)-4-(2,4-dichlorophenyl)-2-thienyl]methyl]-N-methylcycloheptanecarboxamide;
N-[[4-(4-chlorophenyl)-5-(2,4-dichlorophenyl)-2-thienyl]methyl]-1-methylcyclohexanecarboxamide;
4-chloro-N-[[4-(4-chlorophenyl)-5-(2,4-dichlorophenyl)-2-thienyl]methyl]benzamide;
N-[[4-(4-chlorophenyl)-5-(2,4-dichlorophenyl)-2-thienyl]methyl]-4-(trifluoromethyl)benzamide;
1-[[4-(4-chlorophenyl)-5-(2,4-dichlorophenyl)-2-thienyl]methyl]-3-(4-fluorophenyl)urea;
1-(4-bromophenyl)-3-[[4-(4-chlorophenyl)-5-(2,4-dichlorophenyl)-2-thienyl]methyl]urea;
N-[[5-(2,4-dichlorophenyl)-4-(4-methoxyphenyl)-2-thienyl]methyl]bicyclo[2.2.1]heptane-2-carboxamide;
N-[[5-(2,4-dichlorophenyl)-4-(4-methoxyphenyl)-2-thienyl]methyl]-2-propylpentanamide;
N-[[4-(2,4-dichlorophenyl)-5-(4-methoxyphenyl)-2-thienyl]methyl]-2-propylpentanamide;

and their hydrates or their solvates.

The expression leaving group is understood to mean, in the text which follows, a group which can be easily cleaved from a molecule by breaking a heterolytic bond, with a departure of an electron pair. This group can thus be easily replaced by another group during a substitution reaction, for example. Such leaving groups are, for example, halogens or an activated hydroxyl group such as a methanesulfonate, benzenesulfonate, p-toluenesulfonate, triflate, acetate and the like. Examples of leaving groups and references for their preparation are given in "Advances in Organic Chemistry", J. March, 3$^{rd}$ Edition, Wiley Interscience, 1985, p. 310-316.

In accordance with the invention, the compounds of formula (I) can be prepared according to a method which is characterized in that:

a compound of formula:

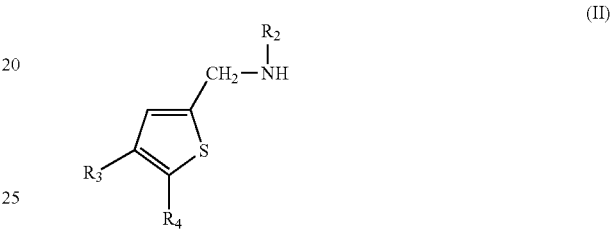

in which R$_2$, R$_3$ and R$_4$ are as defined for a compound of formula (I), is treated:

either with an acid or a functional derivative of this acid or formula:

in which R$_1$ is as defined for a compound of formula (I), when a compound of formula (I) has to be prepared in which —X— represents an —CO— group;

or with a haloformate of formula:

in which Hal represents a halogen atom and Ar represents a phenyl or a 4-nitrophenyl, to give an intermediate compound of formula:

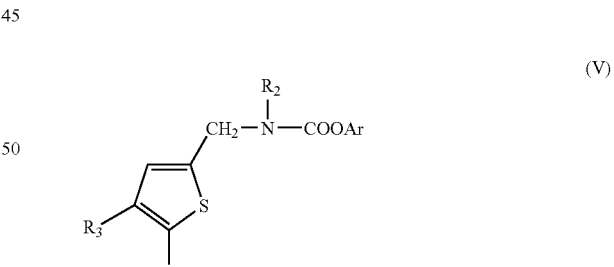

in which R$_2$, R$_3$ and R$_4$ are as defined for a compound of formula (I), which is then reacted with an amine of formula:

in which R$_1$ and R$_5$ are as defined for a compound of formula (I), when a compound of formula (I) has to be prepared in which —X— represents a —CON(R$_5$)— group;

or with an isothiocyanate of formula:

in which $R_1$ is as defined for a compound of formula (I), when a compound of formula (I) has to be prepared in which —X— represents a —CSNH— group.

Where appropriate, a compound of formula (I) in which $R_5$ represents a ($C_1$-$C_3$)alkyl group may be prepared by an alkylation reaction on the corresponding compound of formula (I) in which $R_5$ represents a hydrogen atom.

When a compound of formula (II) is treated with the acid of formula (III) itself, the procedure is carried out in the presence of a coupling agent used in peptide chemistry, such as 1,3-dicyclohexylcarbodiimide or benzotriazol-1-yloxytris(dimethylamino)phosphonium hexafluorophosphate or benzotriazol-1-yloxytris(pyrrolidino)phosphonium hexafluorophosphate or 2-(1H-benzotriazol-1-yl)-1,1,3,3-tetramethyluronium tetrafluoroborate, in the presence of a base such as triethylamine, N,N-diisopropylethylamine or 4-dimethylaminopyridine, in a solvent such as dichloromethane, dichloroethane, N-N-dimethylformamide or tetrahydrofuran at a temperature between −10° C. and the reflux temperature of the solvent.

As a functional derivative of the acid (III), the acid chloride, the anhydride, a mixed anhydride, a $C_1$-$C_4$ alkyl ester in which the alkyl is straight or branched, an activated ester, for example p-nitrophenyl ester, may be used.

Thus, in the method according to the invention, it is also possible to react the chloride of the acid, obtained by reacting thionyl chloride or oxalyl chloride with the acid of formula (III), with the compound of formula (II), in a solvent, such as a chlorinated solvent (dichloromethane, dichloroethane, chloroform for example), an ether (tetrahydrofuran, dioxane for example), or an amide (N,N-dimethylformamide for example) under an inert atmosphere, at a temperature between 0° C. and room temperature, in the presence of a tertiary amine such as triethylamine, N-methylmorpholine or pyridine.

A variant consists in preparing the mixed anhydride of the acid of formula (III) by reacting ethyl chloroformate with the acid of formula (III), in the presence of a base such as triethylamine, and in reacting it with the compound of formula (II), in a solvent such as dichloromethane, under an inert atmosphere, at room temperature, in the presence of a base such as triethylamine.

When a compound of formula (II) is treated with a haloformate of formula (IV), the procedure is carried out in the presence of a base such as triethylamine, in a solvent such as dichloromethane and at a temperature of between 0° C. and room temperature. Next, the intermediate compound of formula (V) thus obtained is reacted with an amine of formula (VI), in a solvent such as dichloromethane, in the presence of a base such as triethylamine and at a temperature between 0° C. and the reflux temperature of the solvent.

According to a variant of the method, it is possible to prepare the compounds of formula (I) in which —X— represents a —CON($R_5$)— group in which $R_5$=H by reacting a compound of formula (II) with an isocyanate of formula $R_1$—N=C=O (VII), in the presence of a base such as triethylamine, in a solvent such as dichloromethane and at a temperature of between room temperature and the reflux temperature of the solvent.

According to another variant of the method, it is possible to prepare the compounds of formula (I) in which —X— represents a —CON($R_5$)— group by reacting a compound of formula (II) with a compound of formula ClCON($R_5$)$R_1$ (VIII) in the presence of a base such as triethylamine, in a solvent such as dichloromethane and at a temperature between 0° C. and room temperature.

According to another variant of the method, it is possible to prepare a compound of formula (I) in which $R_2$ represents a ($C_1$-$C_3$)alkyl by reacting a compound of formula (I) in which $R_2$=H with a ($C_1$-$C_3$)alkyl halide, in the presence of a base such as sodium hydride, in a solvent such as N,N-dimethylformamide and at a temperature between room temperature and the reflux temperature of the solvent.

The compounds of formula (I) thus obtained may be subsequently separated from the reaction medium and purified according to conventional methods, for example by crystallization or chromatography.

The compounds of formula (II) are prepared by reacting a compound of formula:

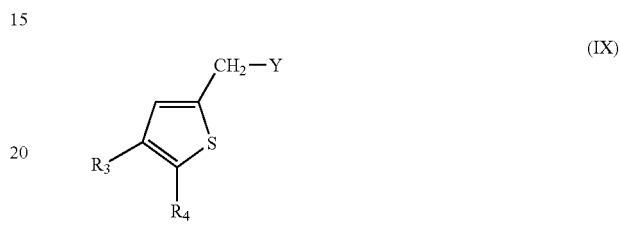

in which $R_3$ and $R_4$ are as defined for a compound of formula (I) and Y represents a leaving group as defined above, preferably a halogen atom or an activated hydroxyl group such as a methanesulfonate, benzenesulfonate, p-toluenesulfonate or triflate group, with a compound of formula:

in which $R_2$ is as defined for a compound of formula (I).

The reaction is carried out in a solvent such as N,N-dimethylformamide, acetonitrile, dichloromethane, toluene or propan-2-ol, and in the presence or in the absence of a base. When a base is used, it is chosen from organic bases such as triethylamine, N,N-diisopropylethylamine or N-methylmorpholine. The reaction is carried out at a temperature of between 0° C. and the reflux temperature of the solvent.

According to a variant, it is also possible to prepare the compound of formula (II) in which $R_2$=H by reacting a compound of formula (IX) in which Y=Cl with 1,3,5,7-tetraazatricyclo[3.3.1$^{3,7}$]decane (or hexamethylenetetramine) followed by hydrolysis with a strong acid such as hydrochloric acid.

According to another variant, it is also possible to prepare a compound of formula (II) in which $R_2$=H by reducing a compound of formula:

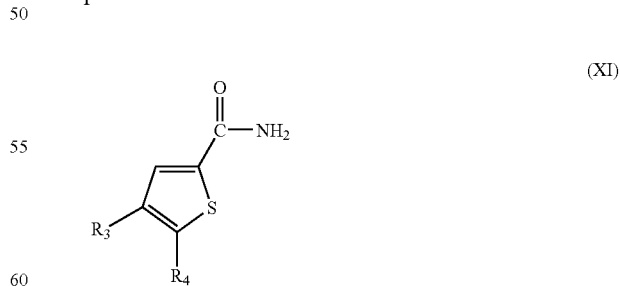

in which $R_3$ and $R_4$ are as defined for a compound of formula (I). The reduction is carried out by means of a reducing agent such as borane in a solvent such as tetrahydrofuran, at a temperature between room temperature and the reflux temperature of the solvent, followed by acid hydrolysis.

The compounds of formula (III) are known.

The compounds of formula (IV), (VI), (VII) and (VIII) are known or are prepared according to known methods.

The compounds of formula (IX) are prepared from the compounds of formula:

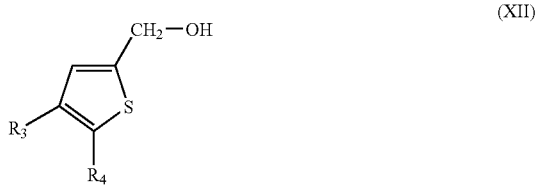

(XII)

in which $R_3$ and $R_4$ are as defined for a compound of formula (I), according to conventional methods cited above.

Thus, for example, when in a compound of formula (IX), Y represents a halogen atom, a compound of formula (XII) is treated with a halogenating agent such as $PCl_5$, $PBr_3$, HBr or $BBr_3$, in a solvent such as dichloromethane and at a temperature between $-10°$ C. and room temperature.

When, in the compound of formula (IX), Y represents a methanesulfonate, a benzenesulfonate, a p-toluenesulfonate or a trifluoromethanesulfonate, a compound of formula (XII) is reacted with a sulfonyl chloride of formula $W-SO_2-Cl$ in which W represents a methyl, a phenyl, a p-tolyl or a trifluoromethyl. The reaction is carried out in the presence of a base such as triethylamine, pyridine or N,N-diisopropylethylamine, in a solvent such as dichloromethane or toluene and at a temperature between $-20°$ C. and the reflux temperature of the solvent.

The compounds of formula (X) are known.

The compounds of formula (XI) are prepared by reacting an acid or a functional derivative of this acid of formula:

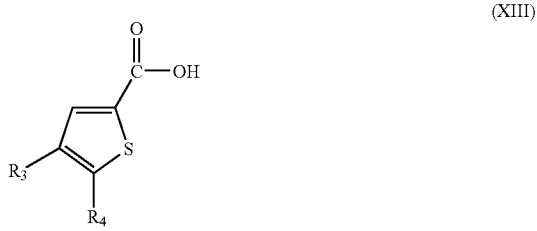

(XIII)

in which $R_3$ and $R_4$ are as defined for a compound of formula (I), with aqueous ammonia.

The compounds of formula (XII) are prepared by a reduction reaction of the compounds of formula:

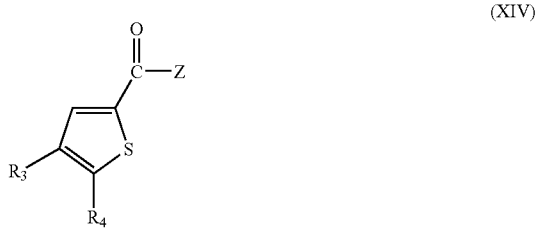

(XIV)

in which $R_3$ and $R_4$ are as defined for a compound of formula (I) and Z represents a hydroxyl or a $(C_1-C_2)$alkoxy.

The reaction is carried out in the presence of a reducing agent such as sodium borohydride or lithium aluminum hydride, in a solvent such as tetrahydrofuran, and at a temperature between $-20°$ C. and room temperature. When a compound of formula (XIV) in which Z=OH is reduced, the acid may be activated beforehand by reaction with ethyl chloroformate in the presence of triethylamine.

The compounds of formula (XIII) or the compounds of formula (XIV) in which Z=OH are prepared by conventional hydrolysis of a compound of formula (XIV) in which Z=$(C_1-C_2)$alkoxy.

The reaction is carried out by hydrolysis in an alkaline medium using, for example, an alkali metal hydroxide such as sodium hydroxide or potassium hydroxide, in a solvent such as water, methanol, 1,2-dimethoxyethane, 1,4-dioxane or a mixture of these solvents, and at a temperature between $0°$ C. and the reflux temperature of the solvent.

The compounds of formula (XIV) in which Z=$(C_1-C_2)$alkoxy are prepared according to SCHEME I below.

SCHEME I

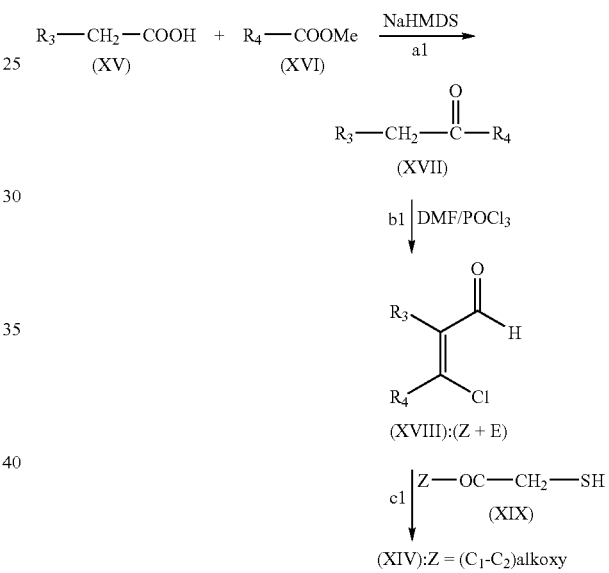

In step a1 of SCHEME I, the reaction of the compound of formula (XV) with a compound of formula (XVI) is carried out in the presence of an alkali metal salt of hexamethyldisilazane such as the sodium salt for example, in a solvent such as tetrahydrofuran and at a temperature of between $-70°$ C. and $0°$ C.

In step b1, the compound of formula (XVII) thus obtained is reacted with the N,N-dimethylformamide/phosphorus oxychloride mixture, in a solvent such as 1,2-dichloroethane and at a temperature between $-10°$ C. and the reflux temperature of the solvent.

The compound (XVIII) thus obtained is reacted in step c1 with the compound (XIX), in the presence of a base such as 1,8-diazabicyclo[5.4.0]undec-7-ene, in a solvent such as acetonitrile and at a temperature between room temperature and the reflux temperature of the solvent.

The compounds of formula (XV), (XVI), (XIX) and (XX) are known or are prepared according to known methods.

The following EXAMPLES describe the preparation of some compounds in accordance with the invention. These examples are not limiting and merely illustrate the present invention. The exemplified compound numbers refer to those given in TABLE I below, which illustrates the chemical structures and the physical properties of a few compounds according to the invention.

In the preparations and in the examples, the following abbreviations are used:
ether: diethyl ether
iso-ether: diisopropyl ether
DMSO: dimethyl sulfoxide
DMF: N,N-dimethylformamide
THF: tetrahydrofuran
TBTU: 2-(1H-benzotriazol-1-yl)-1,1,3,3-tetramethyluronium tetrafluoroborate
DCM: dichloromethane
AcOEt: ethyl acetate
DIPEA: diisopropylethylamine
DBU: 1,8-diazabicyclo[5.4.0]undec-7-ene
TFA: trifluoroacetic acid
Hydrochloric ether 2N: 2N hydrochloric acid solution in diethyl ether
m.p.: melting point
RT: room temperature
b.p.: boiling point
HPLC: high performance liquid chromatography
Silica H: silica 60 H gel marketed by Merck (DARMSTAD)
Buffer solution pH=2: solution of 16.66 g of $KHSO_4$ and 32.32 g of $K_2SO_4$ in 1 liter of water.

The proton nuclear magnetic resonance spectra ($^1$H NMR) are recorded at 200 MHz in DMSO-$d_6$. The chemical shifts δ are expressed as parts per million (ppm). For the interpretation of the spectra, the following abbreviations are used: s: singlet, d: doublet, t: triplet, q: quadruplet, m: unresolved complex, mt: multiplet, bs: broad singlet, dd: doublet of doublet.

The compounds according to the invention are analyzed by LC/UV/MS (liquid chromatography/UV detection/mass spectrometry) coupling. The molecular peak (MH$^+$) and the retention time (tr) in minutes are measured.

Method 1:
There is used a Symmetry C18 column of 2.1×50 mm, 3.5 μm, at 30° C., flow rate 0.4 ml/minute.
The eluent is made up as follows:
solvent A: 0.005% of trifluoroacetic acid in (TFA) in water at pH 3.15;
solvent B: 0.005% of TFA in acetonitrile.
Gradient:

| Time (mn) | % A | % B |
|---|---|---|
| 0 | 100 | 0 |
| 10 | 10 | 90 |
| 15 | 10 | 90 |
| 16 | 100 | 0 |
| 20 | 100 | 0 |

The UV detection is carried out at λ=210 nM and the mass detection in positive ESI chemical ionization mode.

Method 2:
There is used an XTerra MS C18 column of 2.1×50 mm, 3.5 μm, at 30° C., flow rate 0.4 ml/minute.
The eluent is made up as follows:
solvent A: ammonium acetate (AcONH$_4$) 10 mM in water at pH 7;
solvent B: acetonitrile.
Gradient:

| Time (mn) | % A | % B |
|---|---|---|
| 0 | 100 | 0 |
| 10 | 10 | 90 |
| 15 | 10 | 90 |
| 16 | 100 | 0 |
| 20 | 100 | 0 |

The UV detection is carried out at λ=220 nM and the mass detection in positive ESI chemical ionization mode.

Method 3:
There is used an XTerra MS C18 column of 2.1×30 mm; 3.5 μm; at 30° C., flow rate 0.8 ml/minute.
The eluent is made up as follows:
solvent A: 0.025% of trifluoroacetic acid (TFA) in water;
solvent B: 0.025% of TFA in acetonitrile;
Gradient:

| Time (mn) | % A | % B |
|---|---|---|
| 0 | 100 | 0 |
| 2 | 0 | 100 |
| 2.7 | 0 | 100 |
| 2.75 | 100 | 0 |

The UV detection is carried out with a diode array detector between 210 and 400 nM and the mass detection in positive ESI chemical ionization mode.

Preparations

1. Preparation of the Compounds of Formula (XVII)

Preparation 1.1

2-(4-Chlorophenyl)-1-(2,4-dichlorophenyl)ethanone 420 ml of a 2M solution of the sodium salt of hexamethyldisilazane in THF are cooled to −60° C., under a nitrogen atmosphere, 350 ml of THF are added, and then, dropwise, a solution of 57.6 g of 4-chlorophenylacetic acid in 70 ml of THF and the mixture is kept stirred for 1 hour at −60° C. 66 g of methyl 2,4-dichlorobenzoate are then added, dropwise and at −60° C., the mixture is kept stirred for 40 minutes at −60° C. and then the temperature is allowed to rise to 0° C. The reaction mixture is poured over an ice/1 liter of 2N HCl mixture, extracted with ether, the organic phase is washed with a saturated NaHCO$_3$ solution, with water, the organic phase is dried over Na$_2$SO$_4$, the solvent is concentrated under vacuum to a volume of 150 ml, 200 ml of pentane are added and the crystallized product formed is drained. 60 g of the expected compound are obtained.

Preparation 1.2

2-(4-Bromophenyl)-1-(2,4-dichlorophenyl)ethanone 436 ml of a 2M solution of the sodium salt of hexamethyldisilazane in THF are cooled to −60° C., under a nitrogen atmosphere, 400 ml of THF are added, followed dropwise by a solution of 75 g of 4-bromophenylacetic acid in 100 ml of THF and the medium is left for 1 hour 30 minutes with stirring at −70° C. 67.9 g of methyl 2,4-dichlorobenzoate are then added dropwise, the medium is left for 30 minutes, with stirring, and then the temperature is allowed to rise to 5° C. The reaction mixture is poured over an ice/1 liter of 2N HCl mixture, extracted with ether, the organic phase is washed with a saturated NaHCO$_3$ solution, with water, dried over Na$_2$SO$_4$ and the solvent is evaporated under vacuum to a volume of 200 ml, pentane is added and the crystallized product formed is drained. 80 g of the expected compound are obtained.

Preparation 1.3

1-(4-Chlorophenyl)-2-(2,4-dichlorophenyl)ethanone 411 ml of a 2M solution of the sodium salt of hexamethyldisilazane in THF are cooled to −60° C., under a nitrogen atmosphere, 350 ml of THF are added, followed dropwise by a solution of 67.7 g of 2,4-dichlorophenylacetic acid in 70 ml of THF and the mixture is kept stirred for 2 hours while the temperature is maintained below −40° C. 53.5 g of methyl 4-chlorobenzoate are then added dropwise and at −60° C. and the mixture is kept stirred while the temperature is allowed to rise to 10° C. The reaction mixture is poured over an ice/1 liter 2N HCl mixture, the organic phase is washed with a saturated $NaHCO_3$ solution, with water, extracted with ether, the organic phase is dried over $Na_2SO_4$ and the solvent is evaporated under vacuum. The residue is taken up in pentane and the crystallized product formed is drained. 70 g of the expected compound are obtained.

Preparation 1.4

1-(2,4-Dichlorophenyl)-2-(4-methoxyphenyl)ethanone 413 ml of a 2M solution of the sodium salt of hexamethyldisilazane in THF are cooled to −65° C., under a nitrogen atmosphere, 300 ml of THF are added, followed dropwise by a solution of 55 g of 4-methoxyphenylacetic acid in 70 ml of THF and the mixture is kept stirred for 3 hours at a temperature of less than −45° C. 64.5 g of methyl 2,4-dichlorobenzoate are then added dropwise and the mixture is kept stirred while the temperature is allowed to rise to 0° C. The reaction mixture is poured over an ice/1 liter 2N HCl mixture, extracted with ether, the organic phase is washed with a saturated $NaHCO_3$ solution, dried over $Na_2SO_4$ and the solvent is evaporated under vacuum. The residue is chromatographed on silica gel, eluted with heptane and then with the heptane/AcOEt mixture to (90/10; v/v). 29 g of the expected compound are obtained.

2. Preparation of the Compounds of Formula (XVIII)

Preparation 2.1

3-Chloro-2-(4-chlorophenyl)-3-(2,4-dichlorophenyl)acrylaldehyde

A solution of 28.7 ml of DMF in 60 ml of 1,2-dichloroethane is cooled to −5° C., 30 ml of $POCl_3$ are added dropwise and then the mixture is kept stirred while allowing the temperature to rise to RT. A solution of 30 g of the compound obtained in Preparation 1.1 in 300 ml of 1,2-dichloroethane is then added and the mixture is heated at 60° C. overnight. After cooling, the reaction mixture is poured over ice, the pH is brought to 7 by addition of $NaHCO_3$, the mixture is extracted with DCM, the organic phase is dried over $Na_2SO_4$ and the solvent is evaporated under vacuum. The residue is chromatographed under silica gel, eluting with DCM. 35 g of the expected compound are obtained.

Preparation 2.2

2-(4-Bromophenyl)-3-chloro-3-(2,4-dichlorophenyl)acrylaldehyde

A solution of 33.7 ml of DMF in 75 ml of 1,2-dichloroethane is cooled to −5° C., 40.6 ml of $POCl_3$ are added dropwise and then the mixture is kept stirred while the temperature is allowed to rise to RT. A solution of 40 g of the compound obtained in Preparation 1.2 in 300 ml of 1,2-dichloroethane is then added and the mixture is heated under reflux for 48 hours. After cooling, the reaction mixture is poured into 1.5 liters of ice-cold water, the pH is brought to 7 by addition of $NaHCO_3$, the mixture is extracted with DCM, the organic phase is dried over $Na_2SO_4$ and the solvent is evaporated under vacuum. The residue is chromatographed on silica gel, eluting with the gradient of the heptane/DCM mixture from (90/10; v/v) to (50/50; v/v). 39 g of the expected compound are obtained.

Preparation 2.3

3-Chloro-3-(4-chlorophenyl)-2-(2,4-dichlorophenyl)acrylaldehyde

A solution of 28.7 ml of DMF in 60 ml of 1,2-dichloroethane is cooled in an ice bath, 30 ml of $POCl_3$ are added dropwise and then the mixture is kept stirred while the temperature is allowed to rise to RT. A solution of 30 g of the compound obtained in Preparation 1.3 in 300 ml of 1,2-dichloroethane is then added and the mixture is heated overnight at 60° C. After cooling, the reaction mixture is poured over ice, the pH is brought to 7 by addition of $NaHCO_3$, the mixture is extracted with DCM, the organic phase is dried over $Na2SO_4$ and the solvent is evaporated under vacuum. The residue is chromatographed on silica gel, eluting with DCM. 30 g of the expected compound are obtained.

Preparation 2.4

3-Chloro-3-(2,4-dichlorophenyl)-2-(4-methoxyphenyl)acrylaldehyde

A solution of 36.9 ml of DMF in 70 ml of 1,2-dichloroethane is cooled to 0-5° C., 41 ml of $POCl_3$ are added dropwise and then the mixture is kept stirred while the temperature is allowed to rise to RT. A solution of 20 g of the compound obtained in Preparation 1.4 in 200 ml of 1,2-dichloroethane is then added and the mixture is then heated at 40° C. overnight and under reflux for 4 hours. After cooling, the reaction mixture is poured over ice, the mixture is alkalinized by addition of sodium acetate, extracted with DCM, the organic phase is dried over $Na_2SO_4$ and the solvent is evaporated under vacuum. The residue is chromatographed on silica gel, eluting with DCM. 25 g of the expected compound are obtained.

3. Preparations of the compounds of formula (XIV): $Z=(C_1-C_2)$alkoxy

Preparation 3.1

Methyl 4-(4-chlorophenyl)-5-(2,4-dichlorophenyl)thiophene-2-carboxylate 8.53 ml of methyl mercaptoacetate and then 10.51 ml of DBU are added to a solution of 33 g of the compound obtained in Preparation 2.1 in 300 ml of acetonitrile and the mixture is kept stirred overnight at RT. The crystallized product formed is drained and it is dried under vacuum. 22 g of the expected compound are obtained.

Preparation 3.2

Methyl 4-(4-bromophenyl)-5-(2,4-dichlorophenyl)thiophene-2-carboxylate 26.8 ml of methyl mercaptoacetate and then 45.5 ml of DBU are added to a solution of 39 g of the compound obtained in Preparation 2.2 in 300 ml of acetonitrile and the mixture is kept stirred overnight at RT. The precipitated product formed is drained and it is dried under vacuum. 13 g of the expected product are obtained.

Preparation 3.3

Methyl 5-(4-chlorophenyl)4-(2,4-dichlorophenyl)thiophene-2-carboxylate 17.1 ml of methyl mercaptoacetate and then 10 ml of DBU are added to a solution of 30 g of the compound obtained in Preparation 2.3 in 150 ml of acetonitrile and the mixture is kept stirred for 24 hours at RT. 2 ml of DBU are added, the mixture is kept stirred for 2 hours at RT, cooled for 30 minutes on an ice bath and the crystallized product formed is drained. 24 g of the expected compound are obtained.

Preparation 3.4

Methyl 5-(2,4-dichlorophenyl)-4-(4-methoxyphenyl)thiophene-2-carboxylate

A mixture of 10 g of the compound of Preparation 2.4 and 5.76 ml of methyl mercaptoacetate in 100 ml of acetonitrile is heated to 45° C., 4.84 ml of DBU are added dropwise and the mixture is kept stirred while the temperature is allowed to return to room temperature. The reaction mixture is concentrated under vacuum, the residue is taken up in a 0.5N HCl solution, extracted with ether, the organic phase is dried over $Na_2SO_4$ and the solvent is evaporated under vacuum. The residue is chromatographed on silica gel, eluting with heptane and then with the heptane/AcOEt mixture to (80/20; v/v). 6.8 ( of the expected compound are obtained.

4. Preparation of the Compounds of Formula (XII)

Preparation 4.1

[4-(4-Chlorophenyl)-5-(2,4-dichlorophenyl)-2-thienyl]methanol

A suspension of 1.43 g of lithium aluminum hydride in 100 ml of THF is cooled to −20° C., a solution of 10 g of the compound obtained in Preparation 3.1 in 20 ml of THF is added dropwise and the mixture is kept stirred for 1 hour at −20° C. The reaction mixture is hydrolyzed by addition of water until a white cloudiness appears, the inorganic salts are filtered on Celite and the filtrate is concentrated under vacuum. The residue it taken up in pentane, the mixture is kept stirred and the crystallized product formed is drained. 7 g of the expected compound are obtained.

5. Preparation of the Compounds of Formula (IX)

Preparation 5.1

5-(Chloromethyl)-3-(4-chlorophenyl)-2-(2,4-dichlorophenyl)thiophene

A solution of 7 g of the compound obtained in Preparation 4.1 in 80 ml of DCM is cooled to −10° C., 4.14 g of $PCl_5$ are added and the mixture is kept stirred for 24 hours while allowing the temperature to rise to RT. Water is added to the reaction mixture, the mixture is kept stirred for 15 minutes, extracted with AcOEt, the organic phase is dried over $Na_2SO_4$ and the solvent is evaporated under vacuum. The residue is taken up in pentane, the mixture is kept stirred and the crystallized product formed is drained. 6.8 g of the expected compound are obtained.

6. Preparation of the Compounds of Formula (XIII) or of Formula (XIV): Z=OH

Preparation 6.1

4-(4-Bromophenyl)-5-(2,4-dichlorophenyl)thiophene-2-carboxylic acid 24 ml of a 30% NaOH solution are added to a mixture of 16 g of the compound obtained in Preparation 3.2 in 80 ml of 1,2-dimethoxyethane and 40 ml of MeOH and the mixture is kept stirred for 2 hours at RT. The reaction mixture is concentrated under vacuum, the residue is extracted with water, the aqueous phase is washed with ether, the aqueous phase is acidified to pH=2 by addition of a 30% HCl solution, extracted with AcOEt, the organic phase is dried over $MgSO_4$ and the solvent is evaporated under vacuum. 12.4 g of the expected compound are obtained after crystallization from iso-ether.

Preparation 6.2

5-(4-Chlorophenyl)4-(2,4-dichlorophenyl)thiophene-2-carboxylic acid 50 ml of MeOH, 1.5 g of NaOH pellets and a few drops of water are added to a solution of 10 g of the compound obtained in Preparation 3.3 in the minimum of 1,2-dimethoxyethane and then the mixture is heated at 60° C. for 3 hours. The reaction mixture is concentrated under vacuum, the residue is extracted with water, the aqueous phase is washed with ether, the aqueous phase is acidified to pH=2 by addition of a 30% HCl solution, extracted with DCM and the crystallized product formed is drained. 8 g of the expected compound are obtained.

Preparation 6.3

5-(2,4-Dichlorophenyl)-4-(4methoxyphenyl)thiophene-2-carboxylic acid

A mixture of 10 g of the compound obtained in Preparation 3.4 and 2.1 g of KOH in 50 ml of 1,2-dimethoxyethane and 100 ml of 95% EtOH is kept stirred for 5 hours at room temperature. The reaction mixture is concentrated under vacuum, the residue is extracted with water, the aqueous phase is washed with ether, the aqueous phase is acidified to pH=2 by addition of a 30% HCl solution, extracted with ether, the organic phase is dried over $NaSO_4$ and the solvent is evaporated under vacuum. The residue is taken up in iso-ether, pentane is added and the crystallized product formed is drained. 7.5 g of the expected compound are obtained.

7. Preparations of the Compounds of Formula (XI)

Preparation 7.1

4-(4-Bromophenyl)-5-(2,4-dichlorophenyl)thiophene-2-carboxamide

A mixture of 14 g of the compound obtained in Preparation 6.1 and 8.35 ml of thionyl chloride in 140 ml of 1,2-dichloroethane is heated under reflux for 2 hours. The reaction mixture is concentrated under vacuum, the residue is taken up in 1,2-dichloroethane and the solvent is evaporated under vacuum. The acid chloride thus formed is taken up in 150 ml of DCM and this solution is added dropwise to a mixture of 32 ml of a 2M solution of aqueous ammonia in MeOH and 4.4 ml of triethylamine, and then the mixture is kept stirred for 30 minutes. The mixture is concentrated under vacuum and 13.6 g of the expected compound are obtained after crystallization from water and drying under vacuum.

Preparation 7.2

5-(4-Chlorophenyl)-4-(2,4-dichlorophenyl)thiophene-2-carboxamide

A mixture of 8 g of the compound obtained in Preparation 6.2 and 6 ml of thionyl chloride in 80 ml of 1,2-dichloroethane is heated at 80° C. for 3 hours. The reaction mixture is concentrated under vacuum, the residue is taken up in toluene and the solvent is evaporated under vacuum. The acid chloride thus formed is taken up in 50 ml of DCM, this solution is added dropwise to 21 ml of a 2M solution of aqueous ammonia in MeOH and then the mixture is kept stirred for 3 hours at RT. The reaction mixture is concentrated under vacuum, the residue is taken up in an ether/water mixture and the precipitate formed is drained. 5.3 g of the expected compound are obtained.

Preparation 7.3

5-(2,4-Dichlorophenyl)-4-(4-methoxyphenyl)thiophene-2-carboxamide

A mixture of 7.5 g of the compound obtained in Preparation 6.3 and 7.22 ml of thionyl chloride in 100 ml of 1,2-dichloroethane is heated under reflux for 3 hours. The reaction mixture is concentrated under vacuum, the residue is taken up in toluene and the solvent is evaporated under vacuum. The acid chloride thus formed is taken up in 20 ml of DCM and this solution is added dropwise to a mixture of 28.3 ml of a 2M solution of aqueous ammonia in MeOH and 4 ml of triethylamine in 30 ml of DCM cooled beforehand to 0-5° C., and then the mixture is kept stirred while allowing the temperature to rise to room temperature. The reaction mixture is concentrated under vacuum, the residue is taken up in a 0.5 N HCl solution, the mixture is extracted with the ether/AcOEt mixture, the organic phase is dried over $Na_2SO_4$ and the solvents are evaporated under vacuum. The residue is taken up in an ether/iso-ether mixture and the precipitate formed is drained. 6 g of the expected compound are obtained.

8. Preparations of the Compounds of Formula (II)

Preparation 8.1

1-[4-(4-Chlorophenyl)-5-(2,4-dichlorophenyl)-2-thienyl]methanamine hydrochloride A mixture of 6.8 g of the compound obtained in Preparation 5.1, 2.75 g of sodium iodide and 2.95 g of hexamethylenetetramine in 100 ml of EtOH is kept stirred for 48 hours at RT and then the mixture is heated at 60° C. for 3 hours. 28 ml of concentrated HCl are then added and the mixture is heated under reflux for 1 hour. The reaction mixture is filtered and the filtrate is concentrated under vacuum. The residue is taken up in 100 ml of ether, 100 ml of water are added, the mixture is kept stirred for 30 minutes and the precipitate formed is drained. 7 g of the expected compound are obtained.

Preparation 8.2

1-[4-(4-Bromophenyl)-5-(2,4-dichlorophenyl)-2-thienyl]methanamine hydrochloride 150 ml of a 1M solution of borane in THF are added to a solution of 13.5 g of the compound obtained in Preparation 7.1 in 35 ml of THF and then the mixture is heated under reflux for 2 hours. After cooling to RT, 40 ml of MeOH are added dropwise. The reaction mixture is cooled to 5° C., 16 ml of 2N hydrochloric ether are added dropwise, the mixture is kept stirred overnight at RT and the crystallized product formed is drained. 8.2 g of the expected compound are obtained.

Preparation 8.3

1-[5-(4-Chlorophenyl)-4-(2,4-dichlorophenyl)-2-thienyl]methanamine hydrochloride 55.4 ml of a 1M solution of borane in THF are added to a solution of 5.3 g of the compound obtained in Preparation 7.2 in 30 ml of THF and then the mixture is heated under reflux for 15 hours. After cooling to RT, 30 ml of MeOH and then 2N hydrochloric ether are added dropwise and the mixture is concentrated under vacuum. The residue is taken up in AcOEt and the precipitate is drained. 4.2 g of the expected compound are obtained.

Preparation 8.4

1-[5-(2,4-Dichlorophenyl)-4-(4-methoxyphenyl)-2-thienyl]methanamine hydrochloride 63.5 ml of a 1M solution of borane in THF are added to a solution of 6 g of the compound obtained in Preparation 7.3 in 60 ml of THF and then the mixture is heated under reflux for 4 hours. After cooling to room temperature, MeOH is added dropwise until the gaseous emission ceases. The reaction mixture is cooled to 5° C., 20 ml of 2N hydrochloric ether are added and the mixture is kept stirred for 30 minutes. The reaction mixture is concentrated under vacuum to a volume of 15 ml which is added dropwise to an ether/iso-ether mixture (70/70; v/v) and the precipitate formed is drained. 3 g of the expected compound are obtained.

Preparation 8.5

1-[4-(2,4-Dichlorophenyl)-5-(4-methoxyphenyl)-2-thienyl]methanamine hydrochloride This compound is prepared according to the procedures described successively in Preparations 1.4, 2.4, 3.4, 6.3, 7.3 and 8.4.

EXAMPLE 1

Compound No. 1

N-[[4-(4-Chlorophenyl)-5-(2,4-dichlorophenyl)-2-thienyl]methyl]-2-propylpentanamide A mixture of 0.35 g of the compound obtained in Preparation 8.1, 0.125 g of 2-propylpentanoic acid, 0.36 ml of triethylamine and 0.3 g of TBTU in 30 ml of DCM is kept stirred for 48 hours at RT. The reaction mixture is concentrated under vacuum, the residue is taken up in water, extracted with AcOEt, the organic phase is dried over $Na_2SO_4$ and the solvent is evaporated under vacuum. The residue is chromatographed on silica gel, eluting with the gradient of the heptane/AcOEt mixture from (100/1; v/v) to (90/10; v/v). 0.25 g of the expected compound is obtained.

EXAMPLE 2

Compound No. 6

N-Biphenyl-2-yl-N'-[[4-(4-chlorophenyl)-5-(2,4-dichlorophenyl)-2-thienyl]-methyl]urea A mixture of 0.5 g of the compound obtained in Preparation 8.1, 0.25 g of 2-biphenyl isocyanate and 0.52 ml of triethylamine in 20 ml of DCM is kept stirred for 3 hours at RT. The reaction mixture is concentrated under vacuum, the residue is taken up in water, extracted with AcOEt, the organic phase is dried over $Na_2SO_4$ and the solvent is evaporated under vacuum. 0.6 g of the expected compound is obtained after crystallization from ether.

EXAMPLE 3

Compound No. 7

N-[[4-(4-Bromophenyl)-5-(2,4-dichlorophenyl)-2-thienyl]methyl]-4-propylpentanamide A mixture of 0.47 g of the compound obtained in Preparation 8.2, 0.19 ml of 2-propylpentanoic acid, 0.6 ml of triethylamine and 0.4 g of TBTU in 10 ml of DCM is kept stirred for 15 hours at RT. The reaction mixture is concentrated under vacuum, the residue it taken up in water, extracted with ether, the organic phase is washed with water, dried over $Na_2SO_4$ and the solvent is evaporated under vacuum. The residue is chromatographed on silica gel, eluting with the heptane/AcOEt mixture (50/50; v/v). 0.3 g of the expected compound is obtained after crystallization from pentane.

EXAMPLE 4

Compound No. 11

N-[[4-(4-Bromophenyl)-5-(2,4-dichlorophenyl)-2-thienyl]methyl]-N-methylcycloheptanecarboxamide 0.08 g of sodium hydride at 60% in oil is added, under a nitrogen atmosphere, to a mixture of 0.68 g of Compound No. 10 in 7 ml of DMF and the mixture is kept stirred for 1 hour at RT. 0.3 g of methyl iodide is then added and the mixture is kept stirred overnight at RT. The reaction mixture is poured into 50 ml of water, extracted with 30 ml of an AcOEt, the organic phase is dried over $Na_2SO_4$ and the solvent is evaporated under vacuum. 0.43 g of the expected compound is obtained after crystallization from pentane.

EXAMPLE 5

Compound No. 14

N-[[5-(4-Chlorophenyl)-4-(2,4-dichlorophenyl)-2-thienyl]methyl]cycloheptanecarboxamide A mixture of 1 g of the compound obtained in Preparation 8.3, 0.37 g of cycloheptanecarboxylic acid, 1 ml of triethylamine and 0.87 g of TBTU in 40 ml of DCM is kept stirred for 15 hours at RT. The reaction mixture is concentrated under vacuum, the residue is taken up in water, extracted with AcOEt, the organic phase is dried over $Na_2SO_4$ and the solvent is evaporated under vacuum. The residue is dissolved in a minimum of DCM, iso-ether and then pentane are added and the crystallized product formed is drained. 0.8 g of the expected compound is obtained.

EXAMPLE 6

Compounds No. 16 to 34, 58 to 69

The compounds of formula (I) in which —X═—CO— are prepared by combinatory chemistry according to the method described below:

The carboxylic acids of formula (III) are dissolved in DMF at the concentration of 0.25M in the presence of 3 equivalents of DIPEA. 120 μl of these solutions are placed in each 2 ml well and 120 ml of a TBTU solution in DMF at the concentration of 0.25M are added. 300 μl of a solution containing the corresponding compound of formula (II) in DMF at the concentration of 0.1M and 3 equivalents of DIPEA are added to each well. The plates are stirred at RT for 16 hours and then evaporated. The products formed in each well are dissolved by addition of 500 μl of AcOEt, 400 μl of 0.1M $Na_2CO_3$ are added and the plates are stirred. After decantation, 430μl of aqueous phase are removed, 300 μl of 5% NaCl are added and the plates are stirred. 350 μl of aqueous phase are then removed and the compounds obtained are analyzed by LC/UV/MS.

EXAMPLE 7

Compounds No. 35 to 53, 70 to 73

The compounds of formula (I) in which —X═—CONH— or —X═—CSNH— are prepared by combinatory chemistry according to the method described below:

The compounds of formula (II) are dissolved in DMF at a concentration of 0.1M in the presence of 3 equivalents of DIPEA. 300 μl of these solutions are placed in each 2 ml well and 120 μl of a solution containing the isocyanate compound of formula (VII) or the corresponding isothiocyanate compound of formula (XX) in THF at the concentration of 0.25M. are added. The plates are stirred at RT for 16 hours. The products formed in each well are dissolved by addition of 500 μl of AcOEt, 400 μl of 0.1M $Na_2CO_3$ are added and the plates are stirred. After decantation, 430 μl of aqueous phase are removed, 300 μl of 5% NaCl are added and the plates are stirred. After decantation. 350 μl of aqueous phase are removed and the compounds obtained are analyzed by LC/UV/MS.

The table which follows illustrates the chemical structures and the physical properties of a few examples of compounds according to the invention. In this table:

in the column, "method" represents one of the analytical methods used to determine the molecular peak $MH^+$ and the retention time as described above.

"-" means that the compound is not observed by mass spectrometry and the tr corresponds to the tr of the major peak.

Me represent a methyl group.

TABLE 1

(I)

$$CH_2-N(R_2)-X-R_1$$ on thiophene ring with $R_3$, $R_4$ substituents

| Compounds No. | X | $R_1$ | $R_2$ | $R_3$ | $R_4$ | $MH^+$; tr(min) Method NMR |
|---|---|---|---|---|---|---|
| 1 | —C(=O)— | —CH(CH₂CH₂CH₃)₂ | H | 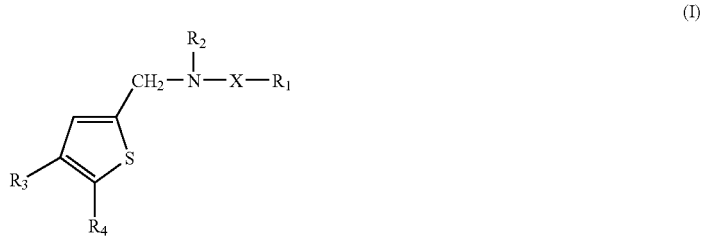 | | 494; 12.19 Method 2 NMR |

TABLE 1-continued
(I)
| Compounds No. | X | R₁ | R₂ | R₃ | R₄ | MH⁺; tr(min) Method NMR |
|---|---|---|---|---|---|---|
| 2 | 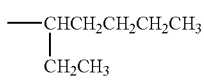 | —CHCH₂CH₂CH₂CH₃<br>CH₂CH₃ | H | 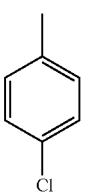 | 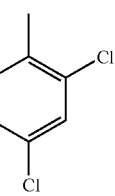 | 494; 12.12<br>Method 1 |
| 3 |  | —CHCH₂CH₂CH₂CH₃<br>CH₃ | H | 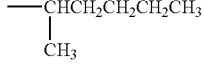 | 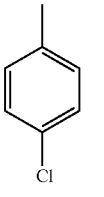 | 480; 11.79<br>Method 1 |
| 4 | 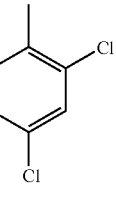 |  | H | 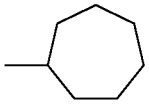 | 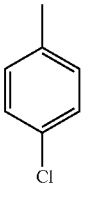 | 492; 12.03<br>Method 1 |
| 5 | 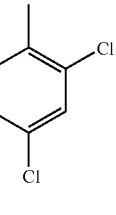 | —CH₂— | H | 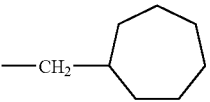 | 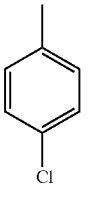 | 506; 12.28<br>Method 2 |
| 6 | 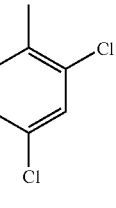 | 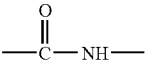 | H | 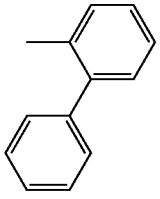 | 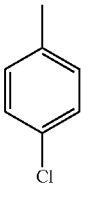 | 563; 12.06<br>Method 2 |
| 7 | 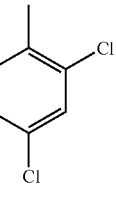 | —CH(CH₂CH₂CH₃)₂ | H |  | 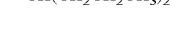 | 538; 12.72<br>Method 1<br>NMR |

TABLE 1-continued
(I)
| Compounds No. | X | $R_1$ | $R_2$ | $R_3$ | $R_4$ | MH+; tr(min) Method NMR |
|---|---|---|---|---|---|---|
| 8 | 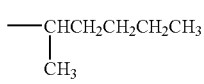 | —CHCH$_2$CH$_2$CH$_2$CH$_3$<br>　　CH$_3$ | H | 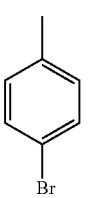 | 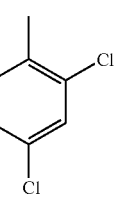 | 524; 12.46<br>Method 1 |
| 9 | 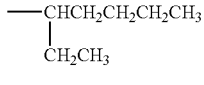 | —CHCH$_2$CH$_2$CH$_2$CH$_3$<br>　　CH$_2$CH$_3$ | H | 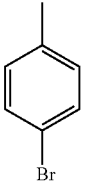 | 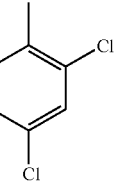 | 538; 12.79<br>Method 1<br>NMR |
| 10 | 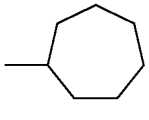 | 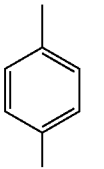 | H | 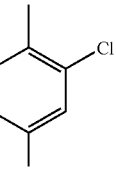 | 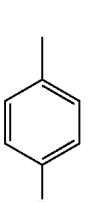 | 536; 12.55<br>Method 1 |
| 11 | 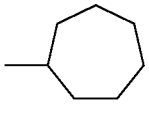 | 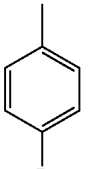 | —CH$_3$ | 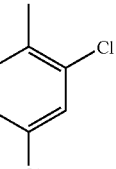 | 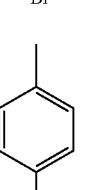 | 550; 13.47<br>Method 1 |
| 12 | 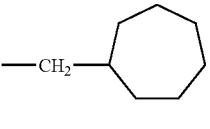 | 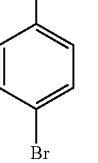 | H | 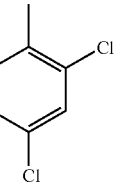 | 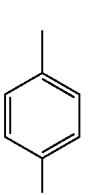 | 550; 12.85<br>Method 1 |
| 13 | 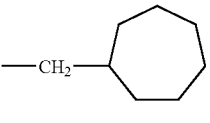 | 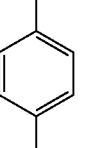 | —CH$_3$ | 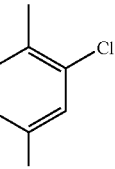 |  | 564; 13.99<br>Method 1 |

TABLE 1-continued
| Compounds No. | X | R₁ | R₂ | R₃ | R₄ | MH⁺; tr(min) Method NMR |
|---|---|---|---|---|---|---|
| 14 | 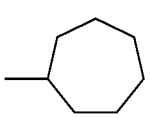 | 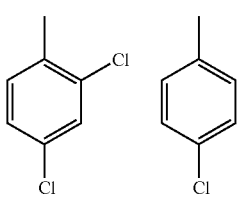 | H | 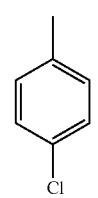 |  | 492; 12.06 Method 2 |
| 15 | 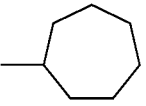 | 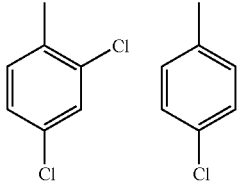 | —CH₃ | 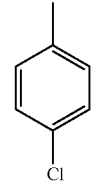 |  | 506; 13.36 Method 1 |
| 16 |  | 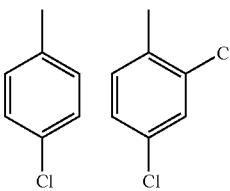 | H | 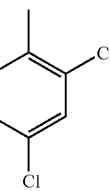 |  | 450; 2.2 Method 3 |
| 17 | 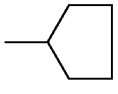 | 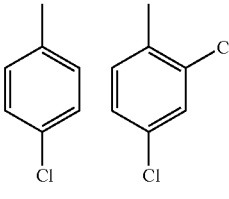 | H | 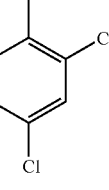 |  | 464; 2.24 Method 3 |
| 18 | 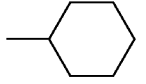 | 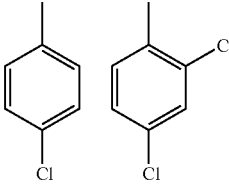 | H | 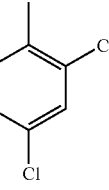 |  | 478; 2.31 Method 3 |
| 19 | 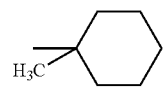 | 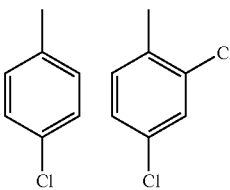 | H | 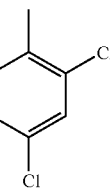 | | 492; 2.31 Method 3 |

TABLE 1-continued
(I)
| Compounds No. | X | R₁ | R₂ | R₃ | R₄ | MH⁺; tr(min) Method NMR |
|---|---|---|---|---|---|---|
| 20 | 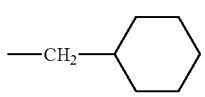 | 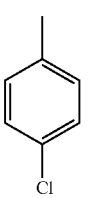 | H | 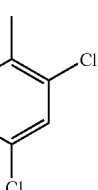 |  | 491.9; 2.35 Method 3 |
| 21 | 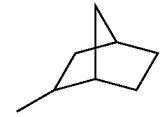 | 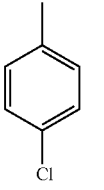 | H | 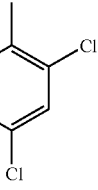 |  | 490; 2.34 Method 3 |
| 22 |  | 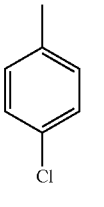 | H | 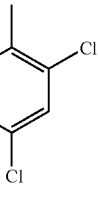 |  | 505.7; 2.59 Method 3 |
| 23 | 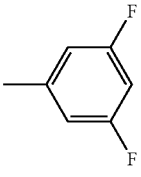 | 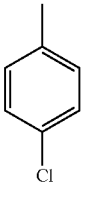 | H | 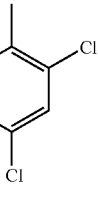 |  | 507.8; 2.53 Method 3 |
| 24 | 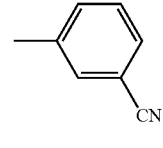 | 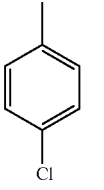 | H | 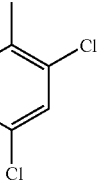 |  | 496.8; 2.51 Method 3 |
| 25 | 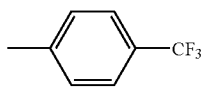 | 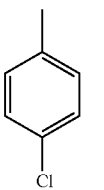 | H | 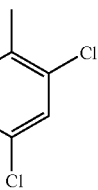 | | 539.8; 2.61 Method 3 |

TABLE 1-continued
(I)
| Compounds No. | X | R₁ | R₂ | R₃ | R₄ | MH⁺; tr(min) Method NMR |
|---|---|---|---|---|---|---|
| 26 | 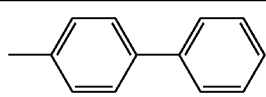 | 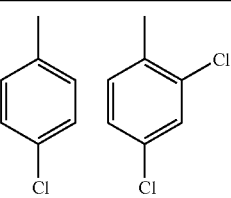 | H | 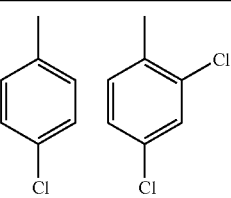 |  | 547.8; 2.61 Method 3 |
| 27 | 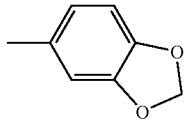 | 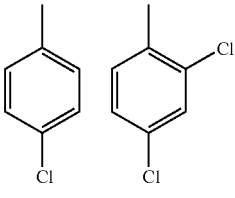 | H | 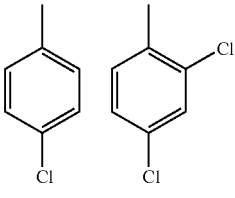 |  | 516; 2.19 Method 3 |
| 28 | 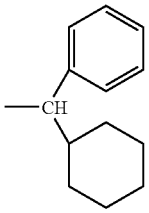 | 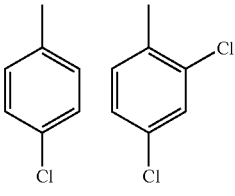 | H | 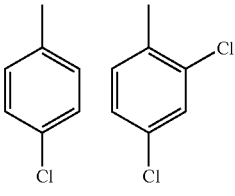 |  | 567.8; 2.59 Method 3 |
| 29 | 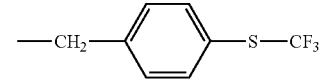 | 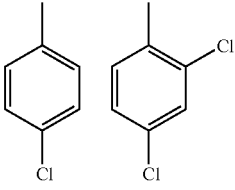 | H | 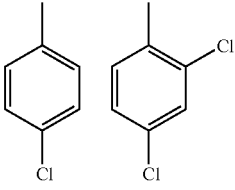 |  | 585.7; 2.57 Method 3 |
| 30 | 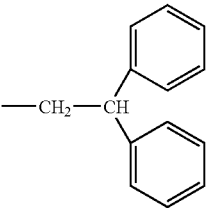 | 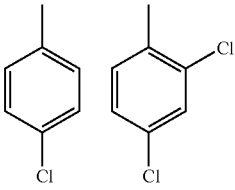 | H | 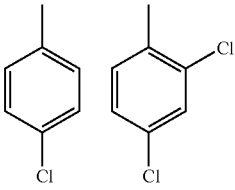 |  | 576; 2.34 Method 3 |
| 31 | 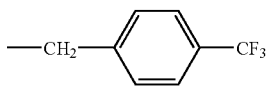 | 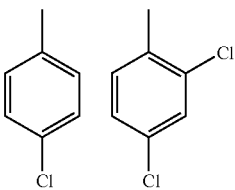 | H | 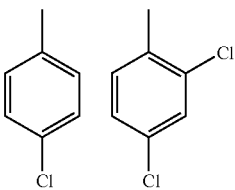 |  | 553.8; 2.58 Method 3 |

TABLE 1-continued
(I)
| Compounds No. | X | R₁ | R₂ | R₃ | R₄ | MH⁺; tr(min) Method NMR |
|---|---|---|---|---|---|---|
| 32 | 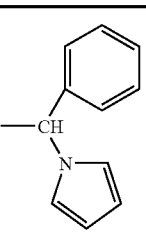 | 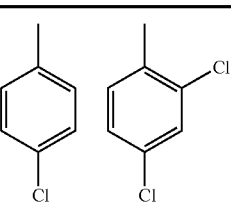 | H |  |  | 550.8; 2.54 Method 3 |
| 33 | 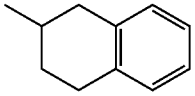 | 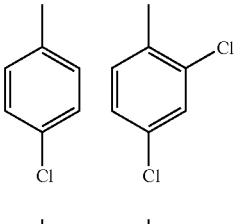 | H |  |  | 550.8; 2.54 Method 3 |
| 34 | 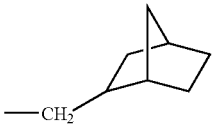 | 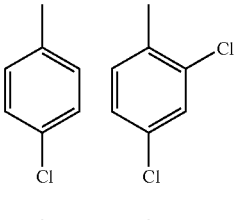 | H |  | 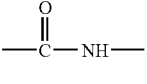 | 503.8; 2.63 Method 3 |
| 35 | 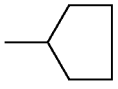 | 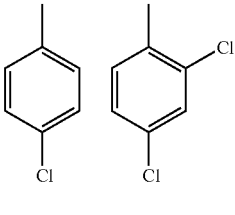 | H |  | 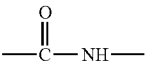 | 479.4; 2.02 Method 3 |
| 36 | 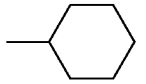 | 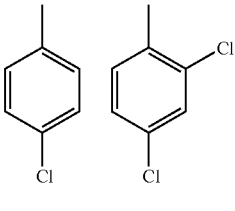 | H |  | 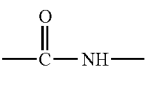 | 493.5; 2.08 Method 3 |
| 37 |  | 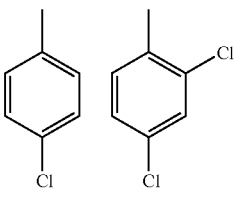 | H |  |  | 505.5; 2.09 Method 3 |

TABLE 1-continued (I)

Structure: CH₂-N(R₂)-X-R₁ attached to thiophene with R₃ and R₄ substituents on the thiophene ring.

| Compounds No. | X | R₁ | R₂ | R₃ | R₄ | MH⁺; tr(min) Method NMR |
|---|---|---|---|---|---|---|
| 38 | —C(O)—NH— | 3-F-phenyl | H | 4-Cl-phenyl | 2,4-diCl-phenyl | 505.4; 2.09 Method 3 |
| 39 | —C(O)—NH— | 4-F-phenyl | H | 4-Cl-phenyl | 2,4-diCl-phenyl | 505.4; 2.07 Method 3 |
| 40 | —C(O)—NH— | 3-OMe-phenyl | H | 4-Cl-phenyl | 2,4-diCl-phenyl | 517.4; 2.06 Method 3 |
| 41 | —C(O)—NH— | 2,5-diF-phenyl | H | 4-Cl-phenyl | 2,4-diCl-phenyl | 523.5; 2.13 Method 3 |
| 42 | —C(O)—NH— | 3-CF₃-phenyl | H | 4-Cl-phenyl | 2,4-diCl-phenyl | 555.4; 2.15 Method 3 |
| 43 | —C(O)—NH— | 4-CF₃-phenyl | H | 4-Cl-phenyl | 2,4-diCl-phenyl | 555.5; 2.16 Method 3 |

TABLE 1-continued (I)

| Compounds No. | X | R₁ | R₂ | R₃ | R₄ | MH⁺; tr(min) Method NMR |
|---|---|---|---|---|---|---|
| 44 | —C(O)—NH— | —CH₂—(2-F-phenyl) | H | 4-Cl-phenyl | 2,4-diCl-phenyl | 519.5; 2.04 Method 3 |
| 45 | —C(O)—NH— | —CH₂—(3-F-phenyl) | H | 4-Cl-phenyl | 2,4-diCl-phenyl | 519.5; 2.04 Method 3 |
| 46 | —C(O)—NH— | —CH₂—(4-F-phenyl) | H | 4-Cl-phenyl | 2,4-diCl-phenyl | 519.4; 2.03 Method 3 |
| 47 | —C(O)—NH— | —CH(phenyl)₂ | H | 4-Cl-phenyl | 2,4-diCl-phenyl | 577.5; 2.13 Method 3 |
| 48 | —C(O)—NH— | 1,2,3,4-tetrahydronaphthalen-2-yl | H | 4-Cl-phenyl | 2,4-diCl-phenyl | 541.5; 2.13 Method 3 |
| 49 | —C(O)—NH— | 4-Br-phenyl | H | 4-Cl-phenyl | 2,4-diCl-phenyl | 565.3; 2.15 Method 3 |

TABLE 1-continued (I)

| Compounds No. | X | R₁ | R₂ | R₃ | R₄ | MH⁺; tr(min) Method NMR |
|---|---|---|---|---|---|---|
| 50 | −C(=O)−NH− | 2-methoxyphenyl, methyl | H | 4-chlorophenyl | 2,4-dichlorophenyl | 517.4; 2.08 Method 3 |
| 51 | −C(=O)−NH− | 5,6,7,8-tetrahydronaphthalen-1-yl, methyl | H | 4-chlorophenyl | 2,4-dichlorophenyl | 541.5; 2.15 Method 3 |
| 52 | −C(=S)−NH− | 3-acetylphenyl, methyl | H | 4-chlorophenyl | 2,4-dichlorophenyl | 544.5; 2.07 Method 3 |
| 53 | −C(=S)−NH− | 4-cyanophenyl, methyl | H | 4-chlorophenyl | 2,4-dichlorophenyl | 528.5; 2.12 Method 3 |
| 54 | −C(=O)− | norbornyl, methyl | H | 4-methoxyphenyl | 2,4-dichlorophenyl | 486.46; 11.77 Method 1 |
| 55 | −C(=O)− | norbornenyl, methyl | H | 4-methoxyphenyl | 2,4-dichlorophenyl | 484.45; 11.30 Method 1 |

TABLE 1-continued
(I)
| Compounds No. | X | R₁ | R₂ | R₃ | R₄ | MH⁺; tr(min) Method NMR |
|---|---|---|---|---|---|---|
| 56 | —C(=O)— | —CH(CH₂CH₂CH₃)₂ | H | 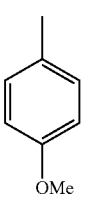 4-MeO-C₆H₄ | 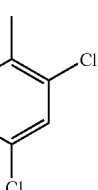 2,4-diCl-C₆H₃ | 490.49; 12.04 Method 1 |
| 57 | —C(=O)— |  cyclohexyl | H | 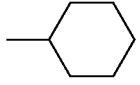 4-MeO-C₆H₄ | 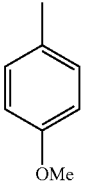 2,4-diCl-C₆H₃ | 488.47; 11.84 Method 1 |
| 58 | —C(=O)— | —CH(CH₂CH₂CH₃)₂ | H | 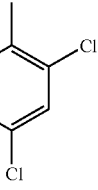 2,4-diCl-C₆H₃ |  4-MeO-C₆H₄ | 490; 2.24 Method 3 |
| 59 | —C(=O)— | 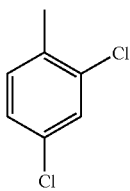 cyclobutyl | H | 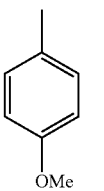 2,4-diCl-C₆H₃ |  4-MeO-C₆H₄ | 446; 2.15 Method 3 |
| 60 | —C(=O)— | 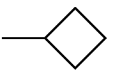 cyclohexyl | H | 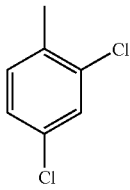 2,4-diCl-C₆H₃ | 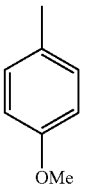 4-MeO-C₆H₄ | 473.9; 2.18 Method 3 |
| 61 | —C(=O)— |  1-methylcyclohexyl | H | 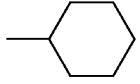 2,4-diCl-C₆H₃ | 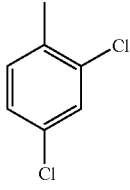 4-MeO-C₆H₄ | 487.9; 2.19 Method 3 |

TABLE 1-continued
(I)
| Compounds No. | X | R₁ | R₂ | R₃ | R₄ | MH⁺; tr(min) Method NMR |
|---|---|---|---|---|---|---|
| 62 |  | 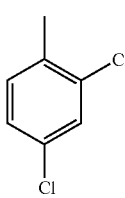 | H | 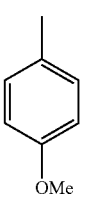 |  | 485.9; 2.21 Method 3 |
| 63 | 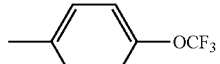 | 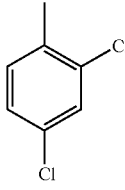 | H | 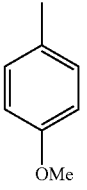 |  | 551.8; 2.22 Method 3 |
| 64 |  | 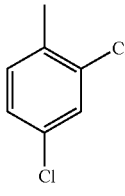 | H | 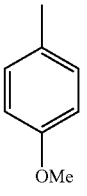 |  | —; 2.11 Method 3 |
| 65 | 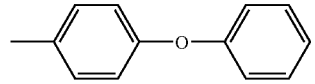 | 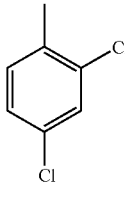 | H | 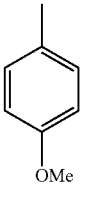 |  | 559.8; 2.31 Method 3 |
| 66 | 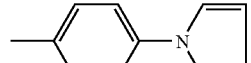 | 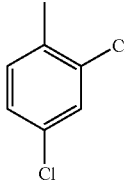 | H | 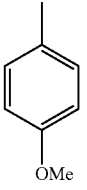 |  | 532.9; 2.20 Method 3 |
| 67 | 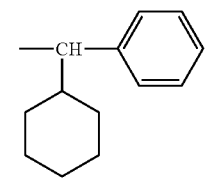 | 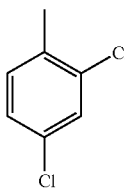 | H | 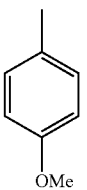 |  | 563.9; 2.41 Method 3 |

TABLE 1-continued (I)

| Compounds No. | X | R₁ | R₂ | R₃ | R₄ | MH⁺; tr(min) Method NMR |
|---|---|---|---|---|---|---|
| 68 | —C(=O)— | —CH₂—CH₂—C₆H₄—CF₃ (4-) | H | 2,4-diCl-C₆H₃ | 4-OMe-C₆H₄ | 563.8; 2.17 Method 3 |
| 69 | —C(=O)— | —CH₂—CH(C₆H₅)₂ | H | 2,4-diCl-C₆H₃ | 4-OMe-C₆H₄ | 571.9; 2.18 Method 3 |
| 70 | —C(=O)—NH— | cyclohexyl | H | 2,4-diCl-C₆H₃ | 4-OMe-C₆H₄ | 489.6; 1.99 Method 3 |
| 71 | —C(=O)—NH— | 4-F-C₆H₄ | H | 2,4-diCl-C₆H₃ | 4-OMe-C₆H₄ | 501.5; 1.98 Method 3 |
| 72 | —C(=O)—NH— | 2-biphenyl | H | 2,4-diCl-C₆H₃ | 4-OMe-C₆H₄ | 559.5; 2.07 Method 3 |

TABLE 1-continued $$\text{(I)}$$

Structure of formula (I): a thiophene ring with substituents $CH_2-N(R_2)-X-R_1$ at position 2, $R_3$ at position 4, and $R_4$ at position 5.

| Compounds No. | X | $R_1$ | $R_2$ | $R_3$ | $R_4$ | $MH^+$; tr(min) Method NMR |
|---|---|---|---|---|---|---|
| 73 | $-\overset{O}{\underset{\|}{C}}-NH-$ | 1-tetrahydronaphthyl (methyl-substituted) | H | 2,4-dichlorophenyl (methyl) | 4-methoxyphenyl (methyl) | 537.6; 2.03 Method 3 |

Compound No. 1: $^1$H NMR: DMSO-$d_6$: δ (ppm): 0.83: t: 6H; 1.05-1.65: m: 8H; 2.20: mt: 1H; 4.81: d: 2H; 7.00-7.55: m: 7H; 7.70: d: 1H; 8.56: t: 1H.
Compound No. 7: $^1$H NMR: DMSO-$d_6$: δ (ppm): 0.83: t: 6H; 1.05-1.65: m: 8H; 2.20: mt: 1H; 4.48: d: 2H; 6.95-7.55: m: 7H; 7.69: d: 1H; 8.55: t: 1H.
Compound No. 9: $^1$H NMR: DMSO-$d_6$: δ (ppm): 0.80: t: 6H; 1.05-1.65: m: 8H; 2.08: mt: 1H; 4.49: d: 2H; 6.95-7.55: m: 7H; 7.69: d: 1H; 8.55: t: 1H.

The compounds of formula (I) possess a very good affinity in vitro ($IC_{50} \leq 5 \times 10^{-7}$M) for the $CB_1$ cannabinoid receptors, under the experimental conditions described by M. Rinaldi-Carmona et al. (FEBS Letters, 1994, 350, 240-244).

The antagonist nature of the compounds of formula (I) has been demonstrated by the results obtained in the adenylate-cyclase inhibition models as described in M. Bouaboula et al., J. Biol. Chem., 1995, 270, 13973-13980, M. Rinaldi-Carmona et al., J. Pharmacol. Exp. Ther., 1996, 278, 871-878 and M. Bouaboula et al., J. Biol. Chem., 1997, 272, 22330-22339.

The toxicity of the compounds of formula (I) is compatible with their use as a medicament.

Thus, according to another of its aspects, the subject of the invention is medicaments which comprise a compound of formula (I), or an addition salt of the latter with a pharmaceutically acceptable acid, or alternatively a solvate or a hydrate of the compound of formula (I).

Thus, the compounds according to the invention may be used in humans or animals, in the treatment or the prevention of diseases involving the $CB_1$ cannabinoid receptors.

For example and without limitation, the compounds of formula (I) are useful as psychotropic medicaments, in particular for the treatment of psychiatric disorders including anxiety, depression, mood disorders, insomnia, delerium disorders, obsessive disorders, psychoses in general, schizophrenia, attention deficit hyperactivity disorder (ADHD), in particular in hyperkinetic children (MBD), and for the treatment of disorders linked to the use of psychotropic substances, in particular in the case of a substance abuse and/or of dependence on a substance, including alcohol dependence and nicotine dependence.

The compounds of formula (I) according to the invention may be used as medicaments for the treatment of migraine, stress, diseases of psychosomatic origin, panic attacks, epileptic attacks, motion disorders, in particular dyskinesia or Parkinson's disease, tremors and dystonia.

The compounds of formula (I) according to the invention may also be used as medicaments in the treatment of memory disorders, cognitive disorders, in particular in the treatment of senile dementia, Alzheimer's disease, and in the treatment of attention or vigilance disorders. Furthermore, the compounds of formula (I) may be useful as neuroprotectants, in the treatment of ischemia, cranial traumas and the treatment of neurodegenerative diseases: including chorea, Huntington's chorea, Tourette's syndrome.

The compounds of formula (I) according to the invention may be used as medicaments in the treatment of pain: neuropathic pain, acute peripheral pain, chronic pain of inflammatory origin.

The compounds of formula (I) according to the invention may be used as medicaments in the treatment of appetite disorders, craving disorders (for sugars, carbohydrates, drugs, alcohol or any appetizing substance) and/or alimentary canal disorders, in particular for the treatment of obesity or of bulimia and for the treatment of type II diabetes or non-insulin-dependent diabetes and for the treatment of dyslipidaemia and of metabolic syndrome. Thus, the compounds of formula (I) according to the invention are useful in the treatment of obesity and of the risks associated with obesity, in particular cardiovascular risks. Furthermore, the compounds of formula (I) according to the invention may be used as medicaments in the treatment of gastrointestinal disorders, diarrhoeal disorders, ulcers, emesis, bladder and urinary disorders, disorders of endocrine origin, cardiovascular disorders, hypotension, haemorrhagic shock, septic shock, chronic cirrhosis of the liver, hepatic steatosis, steatohepatitis, asthma, Raynaud's syndrome, glaucoma, fertility disorders, premature interruption of pregnancy, inflammatory phenomena, immune system diseases, in particular autoimmune and neuroinflammatory diseases such as rheumatoid arthritis, reactive arthritis, diseases causing demyelinization, multiple sclerosis, infectious and viral diseases such as encephalitis, stroke and as medicaments for anticancer therapy, for the treatment of Guillain-Barre syndrome and for the treatment of osteoporosis.

According to the present invention, the compounds of formula (I) are most particularly useful for the treatment of psychotic disorders, in particular schizophrenia, attention deficit hyperactivity disorders (ADHD), in hyperkinetic children (MBD); for the treatment of appetite disorders and obesity; for the treatment of memory and cognitive disorders; for the treatment of alcohol dependence, nicotine dependence, that is to say for withdrawal from alcohol and for smoking cessation.

According to one of its aspects, the present invention relates to the use of a compound of formula (I), of its pharmaceutically acceptable salts and of their solvates or hydrates for the treatment of the disorders and diseases indicated above.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt, a solvate or a hydrate of the said compound, and at least one pharmaceutically acceptable excipient.

The said excipients are chosen according to the pharmaceutical dosage form and the desired mode of administration, from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or its possible salt, solvate or hydrate, may be administered in unit form for administration, as a mixture with conventional pharmaceutical excipients, to animals and to human beings for the prophylaxis or the treatment of the disorders or diseases above.

The appropriate unit forms for administration comprise the forms by the oral route such as tablets, soft or hard gelatin capsules, powders, granules and oral solutions or suspensions, the forms for sublingual, buccal, intratracheal, intraocular or intranasal administration, for administration by inhalation, the forms for topical, transdermal, subcutaneous, intramuscular or intravenous administration, the forms for rectal administration and implants. For topical application, it is possible to use the compounds according to the invention in creams, gels, ointments or lotions.

By way of example, a unit form for administration of a compound according to the invention in tablet form may comprise the following compounds:

| | |
|---|---:|
| Compound according to the invention | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

By the oral route, the dose of active ingredient administered per day may be up to 0.01 to 100 mg/kg, in single or divided doses, preferably 0.02 to 50 mg/kg.

There may be specific cases where higher or lower doses are appropriate, such doses do not depart from the scope of the invention. According to the usual practice, the appropriate dose for each patient is determined by the doctor according to the mode of administration, the weight and the response of the said patient.

The present invention, according to another of its aspects, also relates to a method for treating the pathologies indicated above, which comprises the administration, to a patient, of an effective dose of a compound according to the invention, or one of its pharmaceutically acceptable salts or hydrates or solvates.

The invention claimed is:
1. A compound of the formula (I):

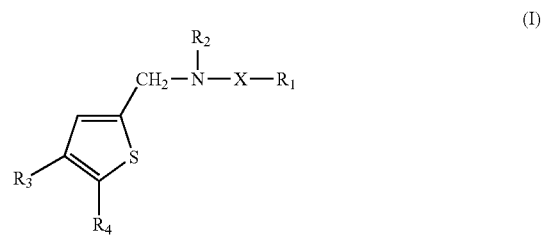

in which:

X represents a group

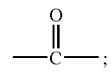

$R_1$ represents:

a $(C_6-C_{12})$alkyl;

a nonaromatic $(C_3-C_{12})$ carbocyclic radical which is unsubstituted or substituted once or several times with a $(C_1-C_4)$alkyl;

a methyl which is substituted with a nonaromatic $C_3-C_{12}$ carbocyclic radical and which is unsubstituted or substituted once or several times on the carbocycle with a $(C_1-C_4)$alkyl;

a phenyl which is mono-, di- or -trisubstituted with substituents independently chosen from a halogen atom, a $(C_1-C_4)$alkoxy, a $(C_1-C_4)$alkylamino, a di-$(C_1-C_4)$alkylamino, a cyano, a trifluoromethyl radical, a trifluoromethoxy radical, an $S(O)_n$Alk group, a $(C_1-C_4)$alkylcarbonyl group, and methylenedioxy;

or substituents chosen from phenyl, phenoxy, pyrrolyl, imidazolyl, pyridyl and pyrazolyl radical, said radicals being unsubstituted or substituted once or several times with a $(C_1-C_4)$alkyl;

a benzyl which is mono- or disubstituted on the phenyl with substituents independently chosen from a halogen atom, a $(C_1-C_4)$alkyl, a $(C_1-C_4)$alkoxy, a trifluoromethyl radical, and (trifluoromethyl)thio radical;

or the phenyl substituted at the alpha-position with one or two similar or different groups chosen from a $(C_1-C_4)$ alkyl, a $(C_3-C_7)$cycloalkyl, or a pyrrolyl radical;

a phenethyl which is unsubstituted or mono- or disubstituted on the phenyl with substituents independently chosen from the halogen atom, a $(C_1-C_4)$alkyl, a $(C_1-C_4)$ alkoxy, and a trifluoromethyl radical;

a 1,2,3,4-tetrahydronaphthyl or a 5,6,7,8-tetrahydronaphthyl which is unsubstituted or mono- or disubstituted with substituents independently chosen from a $(C_1-C_4)$ alkyl, a $(C_1-C_4)$alkoxy and a trifluoromethyl radical;

a benzhydryl; or a benzhydrylmethyl;

$R_2$ represents a hydrogen atom or a $(C_1-C_3)$alkyl;

$R_3$ represents a phenyl which is unsubstituted or mono-, di- or trisubstituted with substituents independently chosen from a halogen atom, a $(C_1-C_4)$alkyl, a $(C_1-C_4)$alkoxy, a trifluoromethyl radical or an $S(O)_n$Alk group;

$R_4$ represents a phenyl which is unsubstituted or mono-, di- or trisubstituted with substituents independently chosen from a halogen atom, a $(C_1-C_4)$alkyl, a $(C_1-C_4)$alkoxy, a trifluoromethyl radical or an $S(O)_n$Alk group;

n represents 0,1 or 2; and

Alk represents a $(C_1-C_4)$alkyl.

2. The compound of formula (I) according to claim 1, in which:

X represents a —CO— group;

$R_1$ represents:

a 1-propylbutyl; a 1-ethylpentyl; a 1-methylpentyl;

a cycloheptyl; a 1- methylcyclopropyl; a cyclobutyl; a cyclopentyl; a cyclohexyl; a 1-methylcyclohexyl; a bicycle[2.2.1]hept-2-yl; a bicyclo [2.2.1]hept-5-en-2-yl;

a cyclohexylmethyl; a cycloheptylmethyl; a bicycle[2.2.1]hept-2-ylmethyl;

a 4-bromophenyl; a 4-chlorophenyl; a 2-fluorophenyl; a 3-fluorophenyl; a 4-fluorophenyl; a 3,5-difluorophenyl; a 2,5-difluorophenyl; a 2- methoxyphenyl; a 3-methoxyphenyl; a 3-cyanophenyl; a 4-cyanophenyl; a 3-(trifluoromethyl)phenyl; a 4-(trifluoromethyl)phenyl: a 4-(trifluoromethoxy)phenyl; a 3-acetylphenyl; a biphenyl-2-yl; a biphenyl-4-yl; a 1,3-benzodioxol-5-yl; a 4-phenoxyphenyl; a 4-(1H-pyrrol-1-yl) phenyl;

a 2-fluorobenzyl; a 3-fluorobenzyl; a 4-fluorobenzyl; a 4-(trifluoromethyl)benzyl; a 4-[(trifluoromethyl)thio]benzyl; an α-cyclohexylbenzyl; an α-(1H -pyrrol-1-yl) benzyl;

a 4-(trifluoromethyl)phenethyl;

a benzhydryl; a benzhydrylmethyl;

a 1,2,3,4-tetrahydronaphth-2-yl; a 1,2,3,4-tetrahydronaphth-1-yl; or a 5,6,7, 8-tetrahydronaphth-1-yl;

$R_2$ represents a hydrogen atom or a methyl;

$R_3$ represents a 4-bromophenyl; a 4-chlorophenyl; a 2,4-dichlorophenyl; or a 4-methoxyphenyl; and $R_4$ represents a 4-chlorophenyl; a 2,4 dichlorophenyl; a 4-methoxyphenyl.

3. The compound of formula (I) according to claim 1, in which:

X represents a —CO— group;

$R_1$ represents:

a 1-propylbutyl; a 1-ethylpentyl; a 1-methylpentyl;

a cycloheptyl;

a cycloheptylmethyl; or a biphenyl-2-yl;

$R_2$ represents a hydrogen atom or a methyl;

$R_3$ represents a 4-bromophenyl; a 4-chlorophenyl; or a 2,4-dichlorophenyl;

$R_4$ represents a 4-chlorophenyl; or a 2,4-dichlorophenyl.

4. The compound of formula (I) according to claim 1, chosen from:

N-[[4-(4-chlorophenyl)-5-(2,4-dichlorophenyl)-2-thienyl]methyl]-2-propylpentanamide;

N-[[4-(4-chlorophenyl)-5-(2,4-dichlorophenyl)-2-thienyl]methyl]-2-ethylhexanamide;

N-[[4-(4-chlorophenyl)-5-(2,4-dichlorophenyl)-2-thienyl]methyl]-2-methylhexanamide;

N-[[4-(4-chlorophenyl)-5-(2,4-dichlorophenyl)-2-thienyl]methyl]-cycloheptanecarboxamide;

N-[[4-(4-chlorophenyl)-5-(2,4-dichlorophenyl)-2-thienyl]methyl]-2-cycloheptylacetamide;

N-[[4-(4-bromophenyl)-5-(2,4-dichlorophenyl)-2-thienyl]methyl]-2-propylpentanamide;

N-[[4-(4-bromophenyl)-5-(2,4-dichlorophenyl)-2-thienyl]methyl]-2-methylhexanamide;

N-[[4-(4-bromophenyl)-5-(2,4-dichlorophenyl)-2-thienyl]methyl]-2-ethylhexanamide;

N-[[4-(4-bromophenyl)-5-(2,4-dichlorophenyl)-2-thienyl]methyl]-cycloheptanecarboxamide;

N-[[4-(4-bromophenyl)-5-(2,4-dichlorophenyl)-2-thienyl]methyl]-N -methylcycloheptanecarboxamide;

N-[[4-(4-bromophenyl)-5-(2,4-dichlorophenyl)-2-thienyl]methyl]-2-cycloheptylacetamide;

N-[[4-(4-bromophenyl)-5-(2,4-dichlorophenyl)-2-thienyl]methyl]-2-cycloheptyl-N-methylacetamide;

N-[[5-(4-chlorophenyl)-4-(2,4-dichlorophenyl)-2-thienyl]methyl]-cycloheptanecarboxamide;

N-[[5-(4-chlorophenyl)-4-(2,4-dichlorophenyl)-2-thienyl]methyl]-N -methylcycloheptanecarboxamide;

N-[[4-(4-chlorophenyl)-5-(2,4-dichlorophenyl)-2-thienyl]methyl]-1-methylcyclohexanecarboxamide;

4-chloro-N-[[4-(4-chlorophenyl)-5-(2,4-dichlorophenyl)-2-thienyl]methyl]benzamide;

N-[[4-(4-chlorophenyl)-5-(2,4-dichlorophenyl)-2-thienyl]methyl]-4-(trifluoromethyl)benzamide;

N-[[5-(2,4-dichlorophenyl)-4-(4-methoxyphenyl)-2-thienyl]methyl]bicyclo [2.2.1]heptane-2-carboxamide;

N-[[5-(2,4-dichlorophenyl)-4-(4-methoxyphenyl)-2-thienyl]methyl]-2-propylpentanamide; and N-[[4-(2,4-dichlorophenyl)-5-(4-methoxyphenyl)-2-thienyl]methyl]-2-propylpentanamide.

5. A method for preparing the compounds of formula (I) according to claim 1, comprising:

treating a compound of formula (II):

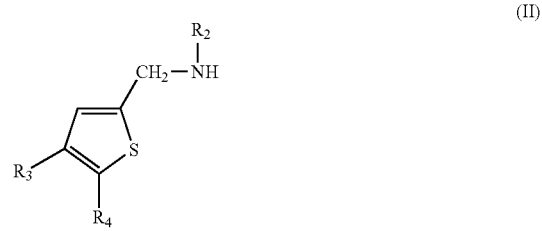

(II)

in which $R_2$, $R_3$ and $R_4$ are as defined for a compound of formula (I) in claim 1, either with an acid of formula (III) or a functional derivative of this acid:

HOOC—$R_1$ (III)

in which $R_1$ is as defined for a compound of formula (I) in claim 1.

6. A pharmaceutical composition comprising a compound of formula (I) according to claim 1 and at least one pharmaceutically acceptable excipient.

7. A pharmaceutical composition comprising a compound of formula (I) according to claim 2 and at least one pharmaceutically acceptable excipient.

8. A pharmaceutical composition comprising a compound of formula (I) according to claim 3 and at least one pharmaceutically acceptable excipient.

9. A pharmaceutical composition comprising a compound of formula (I) according to claim 4 and at least one pharmaceutically acceptable excipient.

* * * * *

UNITED STATES PATENT AND TRADEMARK OFFICE
CERTIFICATE OF CORRECTION

PATENT NO. : 7,687,537 B2
APPLICATION NO. : 11/832162
DATED : March 30, 2010
INVENTOR(S) : Jean-Philippe Ducoux et al.

It is certified that error appears in the above-identified patent and that said Letters Patent is hereby corrected as shown below:

On the first page, in field (56), in column 2, under "Other Publications", line 1, delete "Chewla" and insert -- Chawla --, therefor.

In column 3, line 23, after "and" delete "to".

In column 15, line 16, delete "(" and insert -- g --, therefor.

In column 46, line 40, delete "Tourrette's" and insert -- Tourette's --, therefor.

In column 49, line 19, in claim 2, delete "bicycle" and insert -- bicyclo --, therefor.

In column 49, line 21, in claim 2, delete "bicycle" and insert -- bicyclo --, therefor.

In column 50, line 10, in claim 4, delete "-N -" and insert -- -N- --, therefor.

Signed and Sealed this
Thirty-first Day of May, 2011

David J. Kappos
*Director of the United States Patent and Trademark Office*